(12) United States Patent
Hart et al.

(10) Patent No.: US 6,395,021 B1
(45) Date of Patent: May 28, 2002

(54) URETERAL STENT SYSTEM APPARATUS AND METHOD

(75) Inventors: Charles C. Hart, Huntington Beach, CA (US); Ralph V. Clayman, St. Louis, MO (US); John R. Brustad, Dana Point, CA (US); Frans Vandenbroek, Rancho Santa Margarita, CA (US); Richard C. Ewers, Huntington Beach, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 09/303,113

(22) Filed: Apr. 30, 1999

Related U.S. Application Data

(63) Continuation-in-part of application No. 09/109,355, filed on Jul. 2, 1998, now abandoned, which is a continuation-in-part of application No. 08/806,337, filed on Feb. 26, 1997.

(51) Int. Cl.$^7$ .................................................. A61F 2/06
(52) U.S. Cl. ........................... 623/1.15; 623/1.2; 604/8
(58) Field of Search ................................ 623/1.15, 1.2; 604/527, 8

(56) References Cited

U.S. PATENT DOCUMENTS

| | | | | |
|---|---|---|---|---|
| 2,285,980 A | * | 6/1942 | Jeckel | |
| 3,938,529 A | * | 2/1976 | Gibbons | |
| 4,334,327 A | | 6/1982 | Lyman et al. ...................... 3/1 |
| 4,580,568 A | | 4/1986 | Gianturco .................. 128/345 |
| 4,643,716 A | | 2/1987 | Drach .......................... 604/8 |
| 4,787,884 A | | 11/1988 | Goldberg ....................... 604/8 |
| 4,886,062 A | | 12/1989 | Wiktor ....................... 128/343 |
| 4,913,683 A | | 4/1990 | Gregory ........................ 604/8 |
| 4,931,037 A | | 6/1990 | Wetterman .................... 604/8 |
| 4,957,479 A | | 9/1990 | Roemer ........................ 604/8 |
| 5,026,377 A | | 6/1991 | Burton et al. ............... 606/108 |
| 5,041,092 A | | 8/1991 | Barwick ..................... 604/104 |
| 5,078,720 A | | 1/1992 | Burton et al. ............... 606/108 |
| 5,116,309 A | | 5/1992 | Coll ............................ 604/8 |
| 5,282,784 A | | 2/1994 | Willard ........................ 604/8 |
| 5,306,294 A | | 4/1994 | Winston et al. ................ 623/1 |
| 5,364,340 A | | 11/1994 | Coll ............................ 604/8 |
| 5,401,257 A | | 3/1995 | Chevalier, Jr. et al. ..... 604/265 |
| 5,409,019 A | | 4/1995 | Wilk .......................... 128/898 |
| 5,476,505 A | | 12/1995 | Limon ......................... 623/1 |
| 5,507,767 A | | 4/1996 | Maeda et al. ............... 606/198 |
| 5,575,818 A | * | 11/1996 | Pinchuk ....................... 623/1 |
| 6,017,335 A | * | 1/2000 | Burnham .................... 604/282 |
| 6,090,099 A | * | 7/2000 | Samson er al. ............. 604/527 |

OTHER PUBLICATIONS

"Evaluation of A Chronic Indwelling Prototype Mesh Ureteral Stent In a Porcine Model", Owelny et al., Journal of Urology, vol. 163, No. 4, Supplement, Wednesday May 3, 2000, Section 1416.

\* cited by examiner

Primary Examiner—Michael H. Thaler
(74) Attorney, Agent, or Firm—Richard L. Myers

(57) ABSTRACT

A stent having an elongate tubular configuration is formed of a plurality of elongate elements interwoven or braided to form a tubular configuration. The elements may be relatively strong and rigid, but movable relative to each other within the weave or braid in order to provide the stent with generally soft characteristics. The elements may be formed of different materials, such as an absorbent material permitting the stent to be doped with materials such as drugs and chemicals. Even the absorbency can be controlled and varied to provide a predetermined time-release of the absorbent.

16 Claims, 27 Drawing Sheets

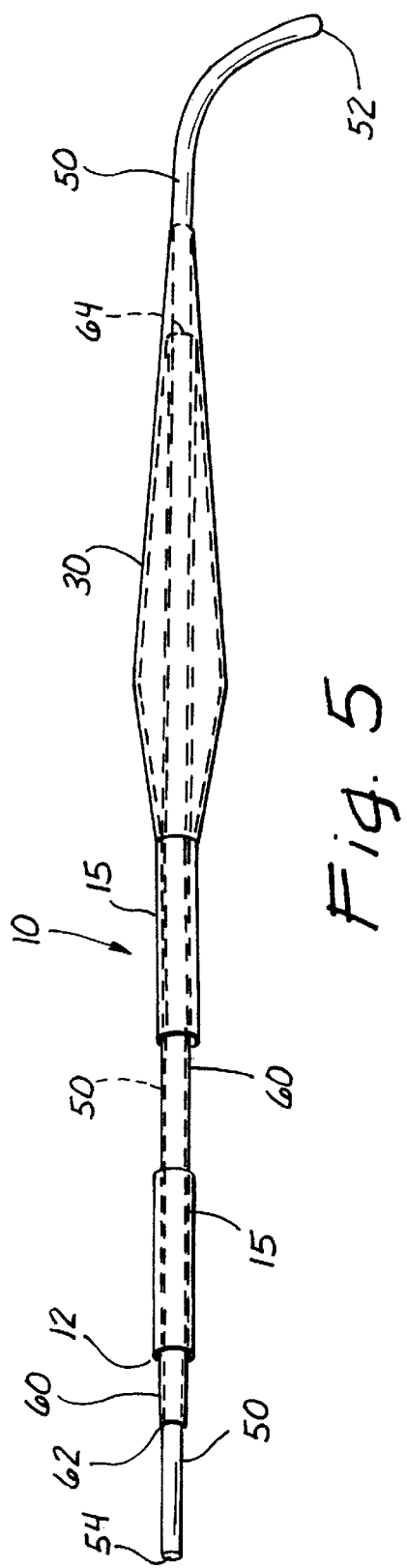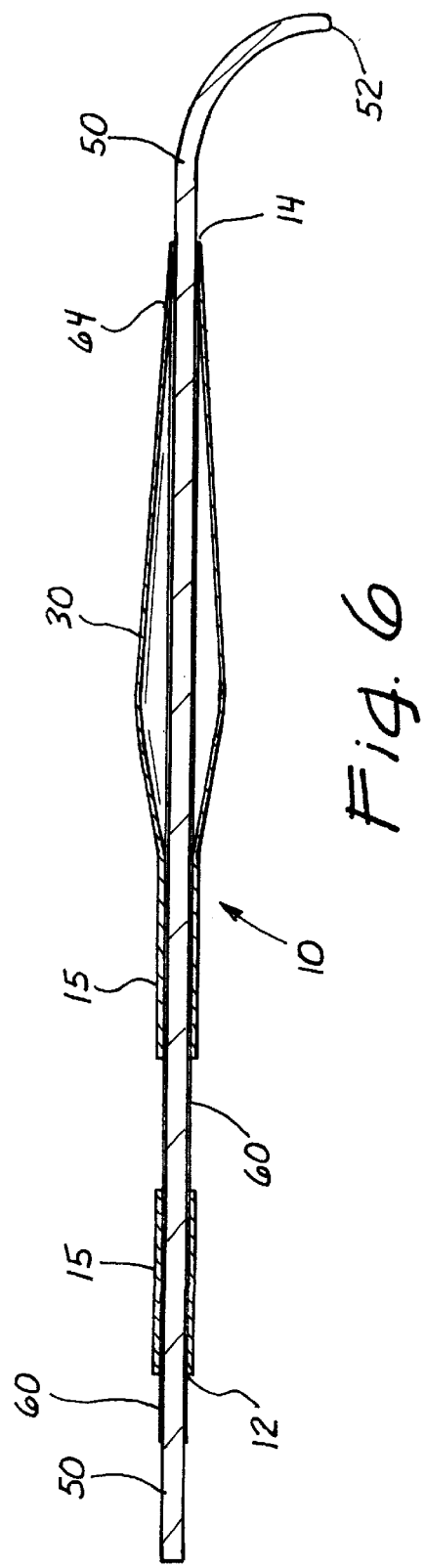

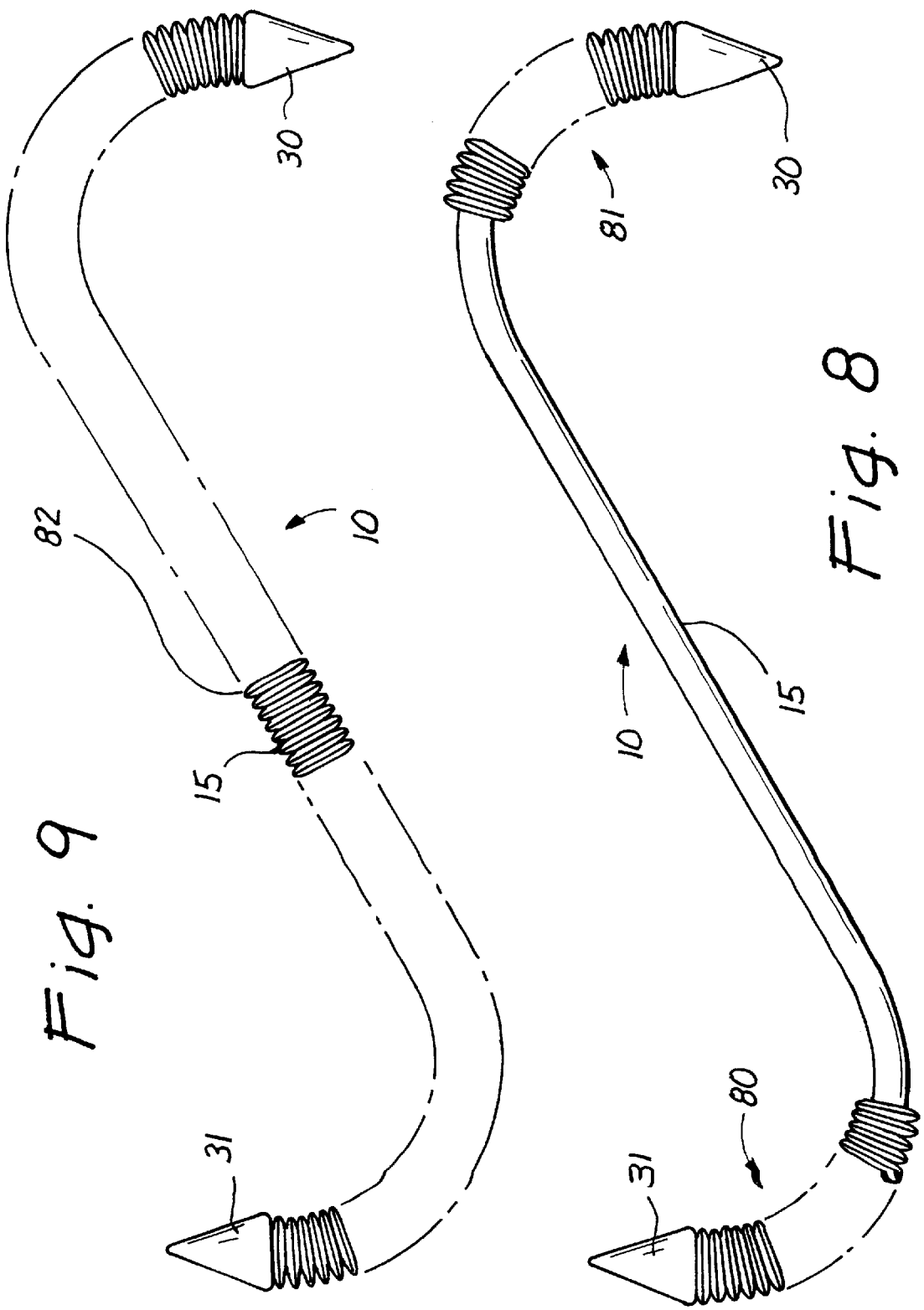

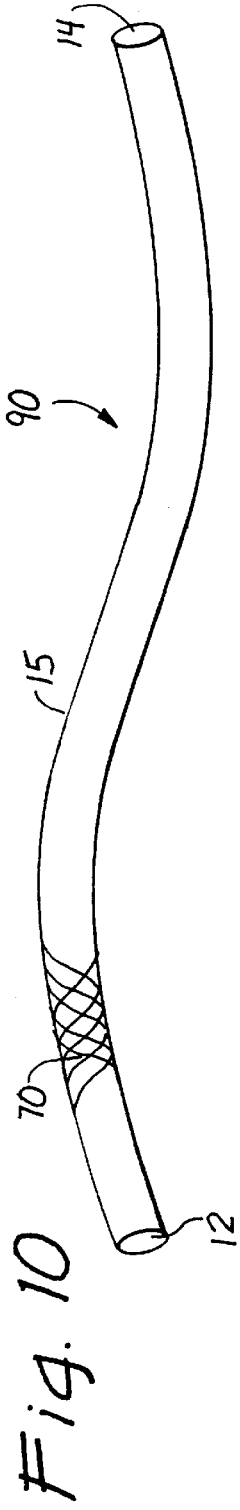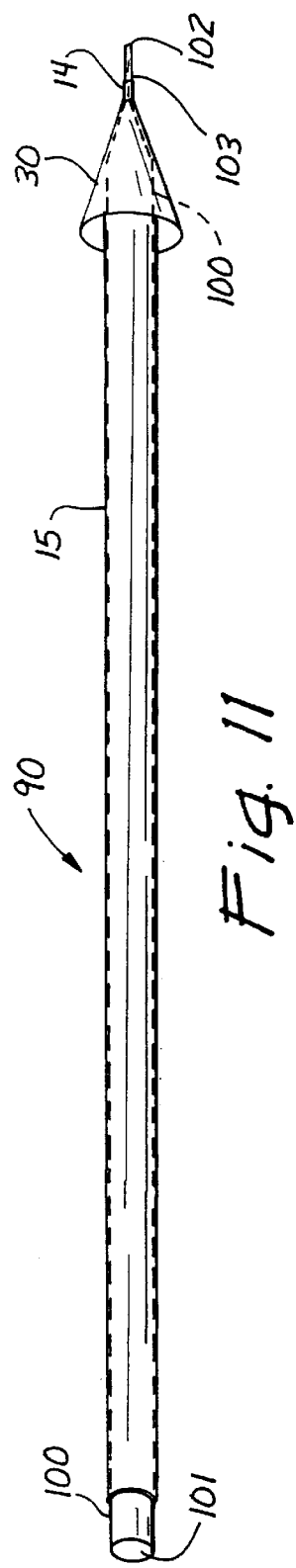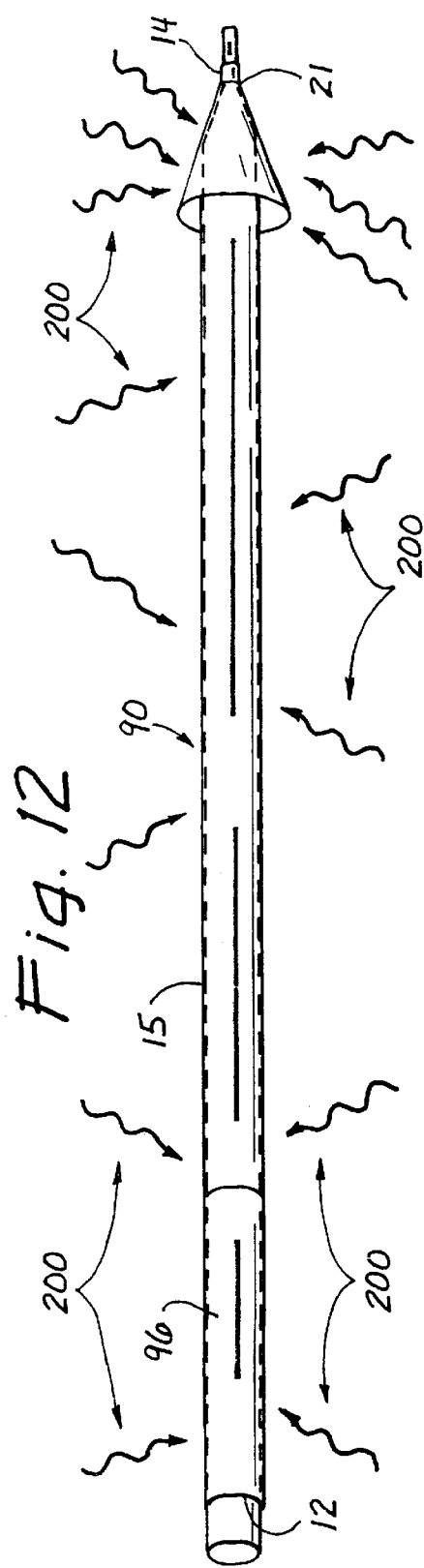

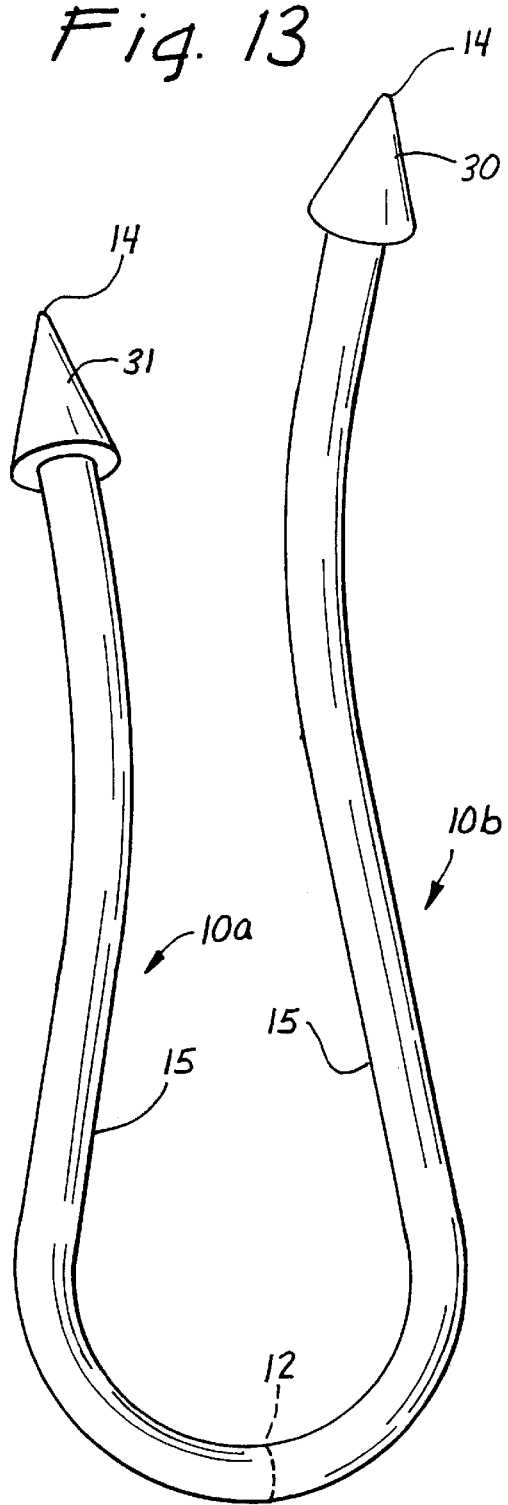
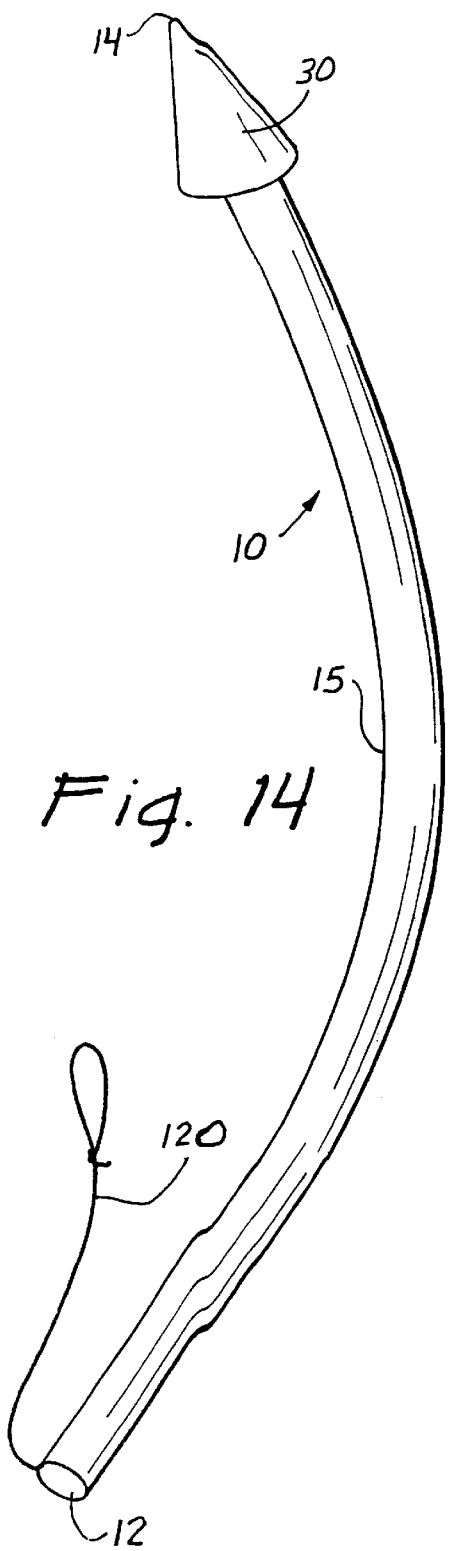

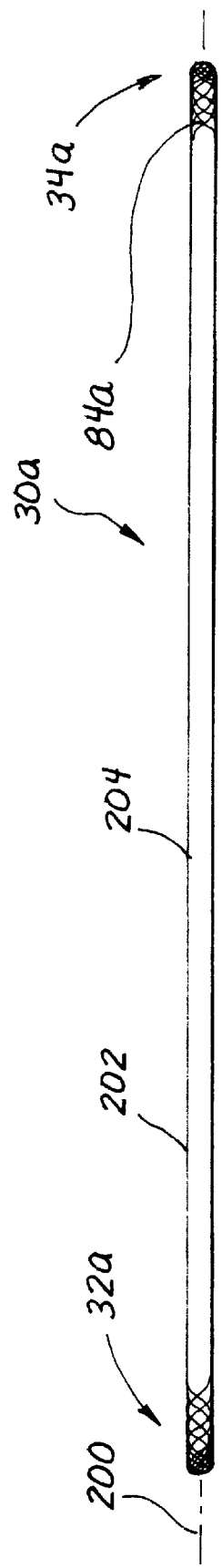
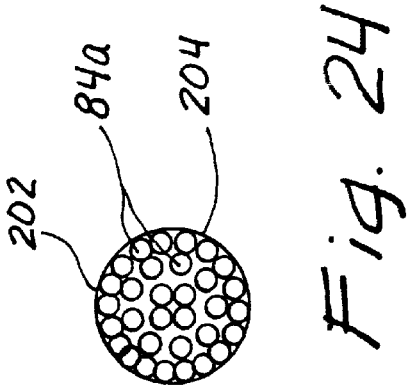

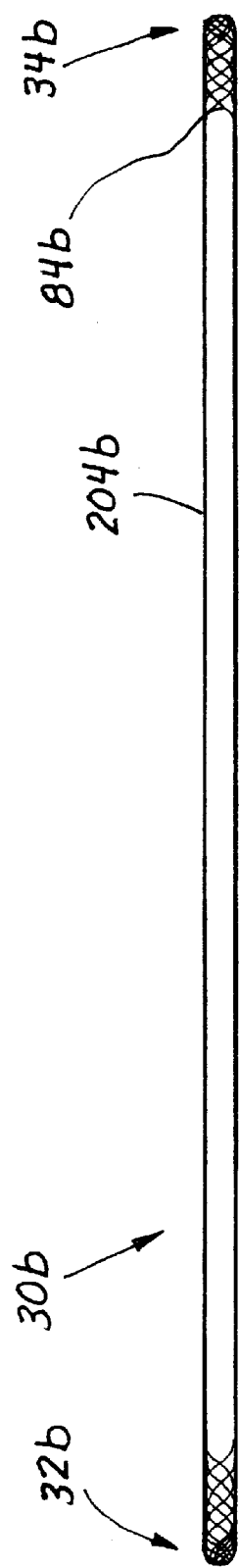
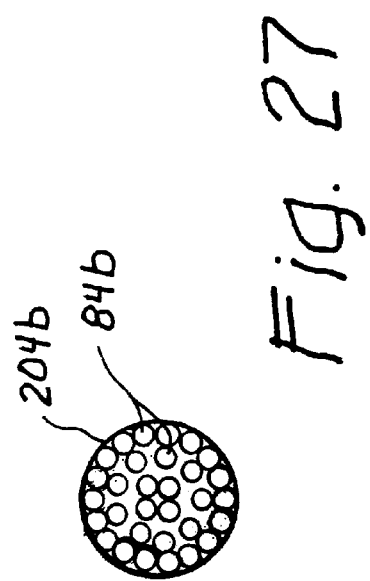
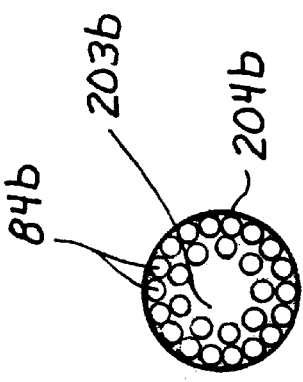

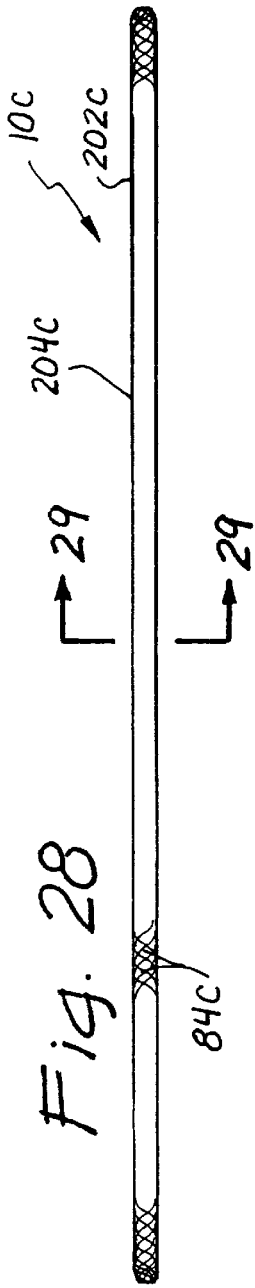
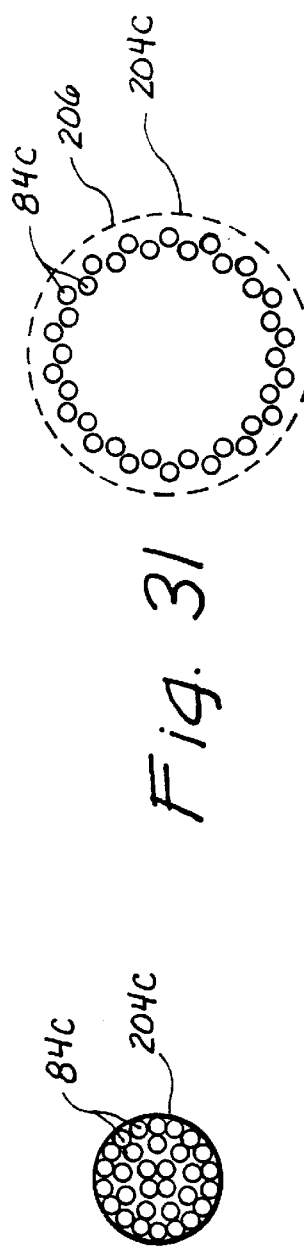
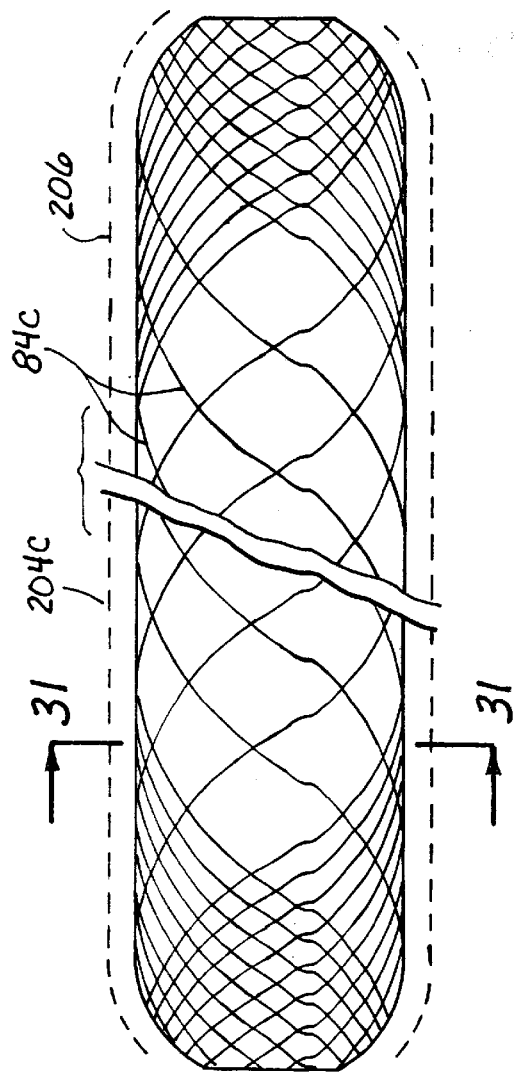
Fig. 28
Fig. 29
Fig. 31
Fig. 30

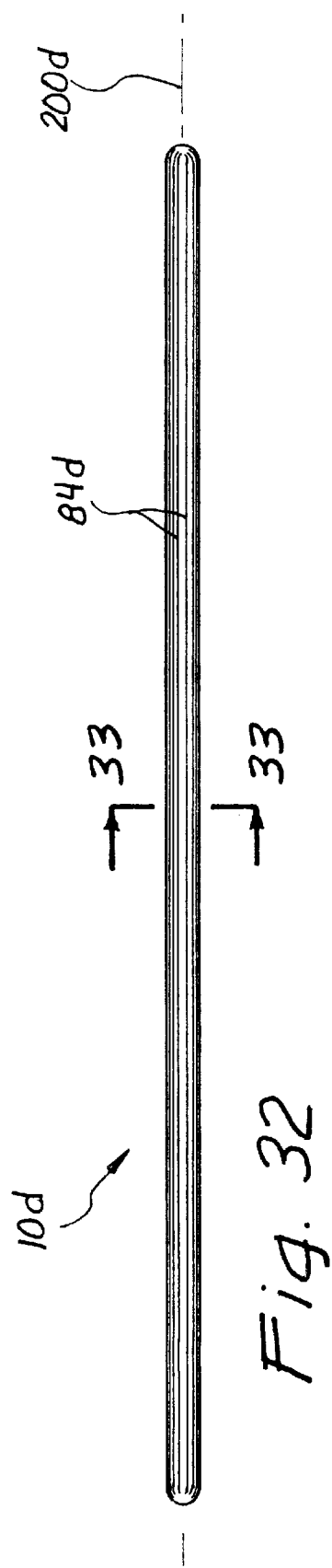
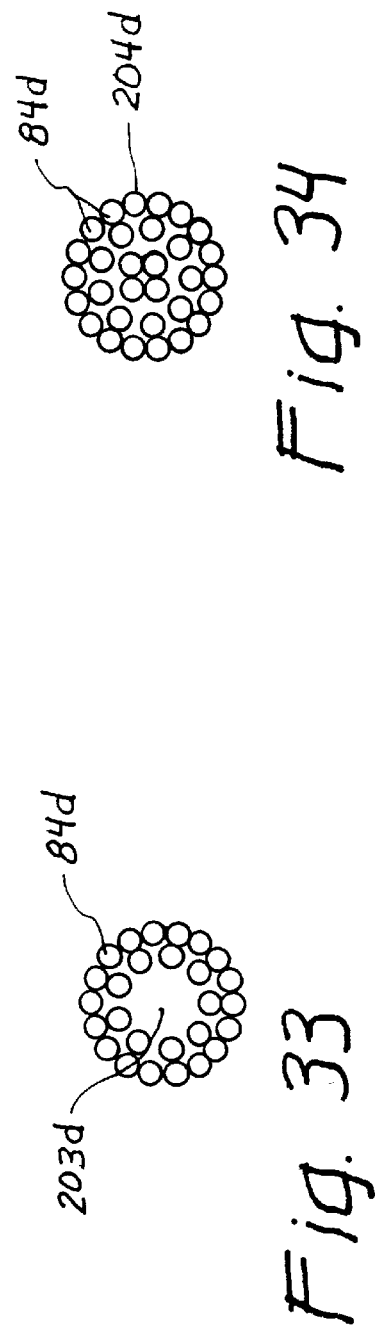

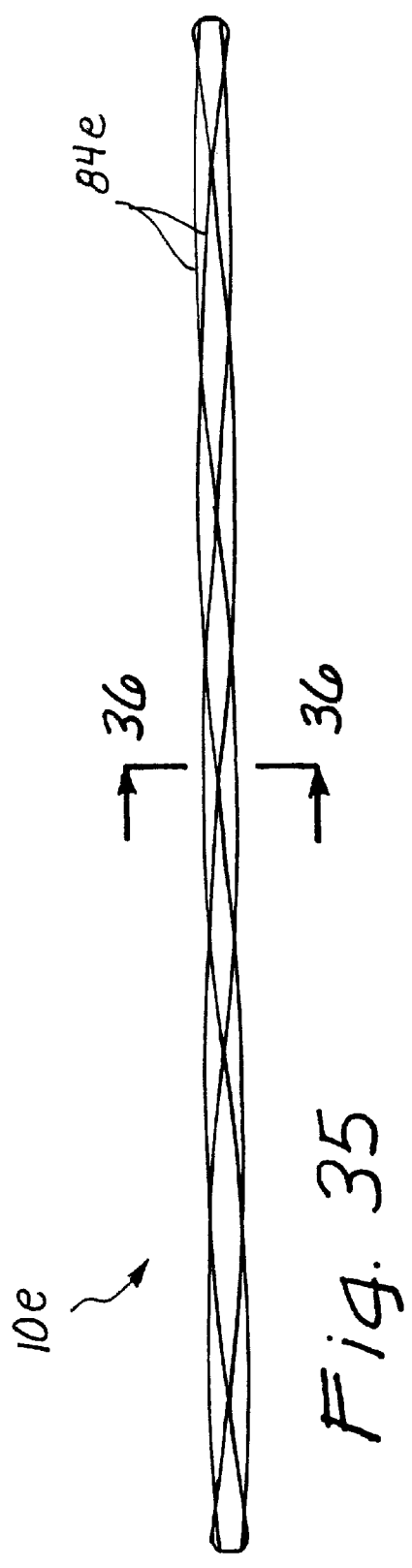
Fig. 35
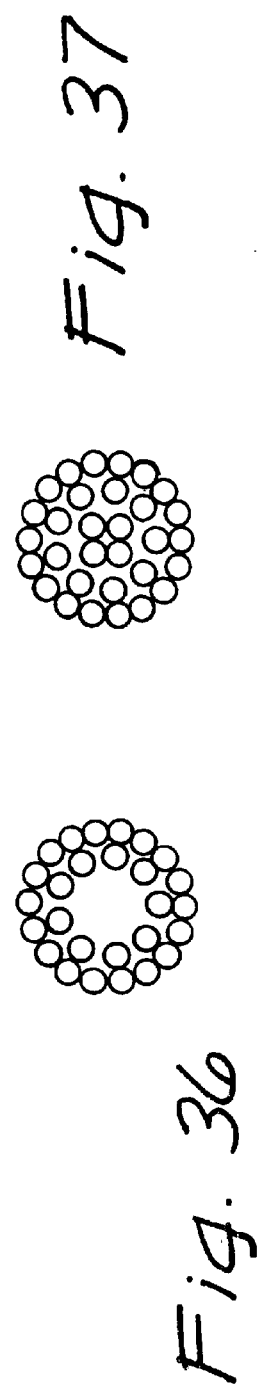
Fig. 37
Fig. 36

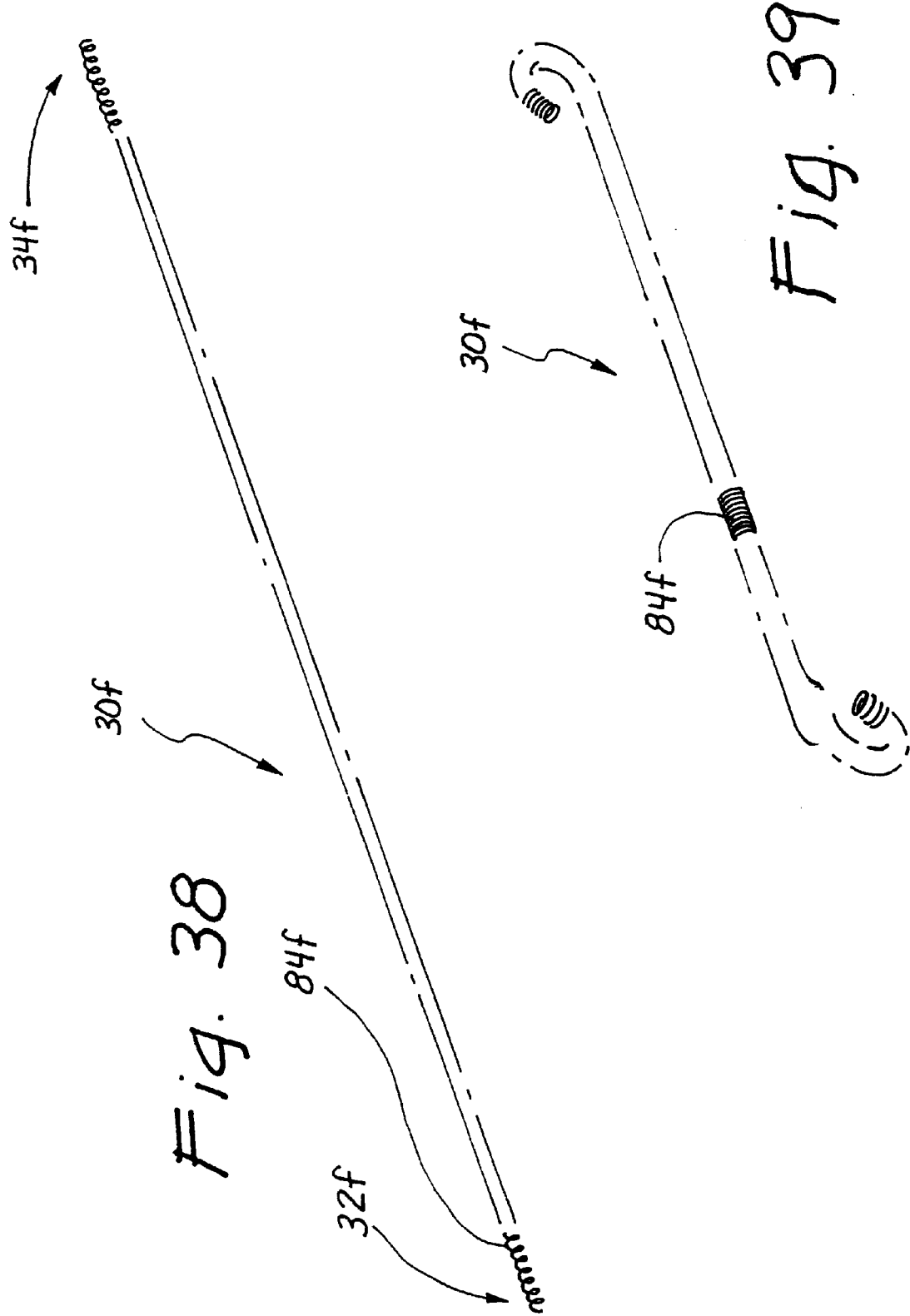

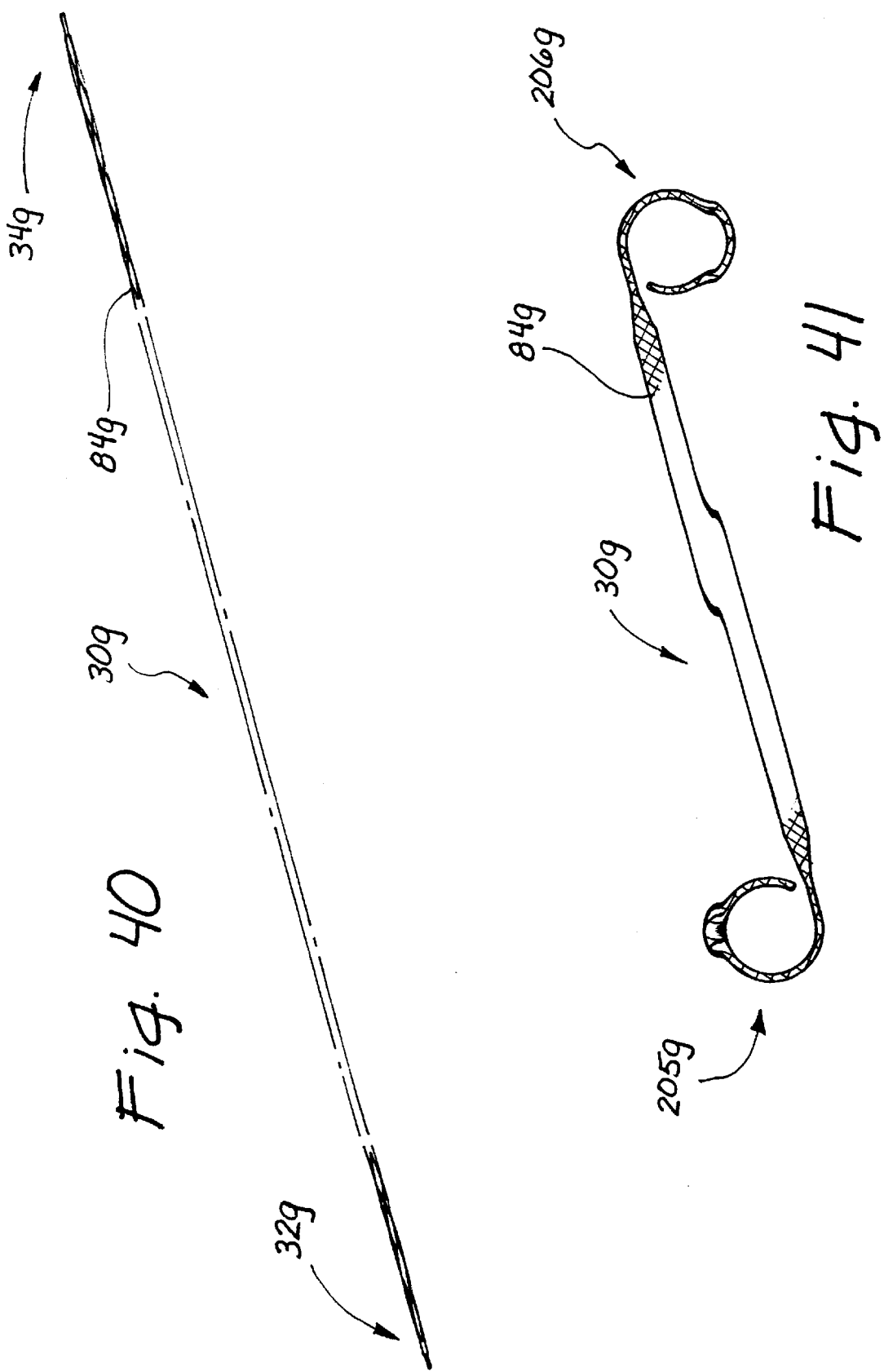

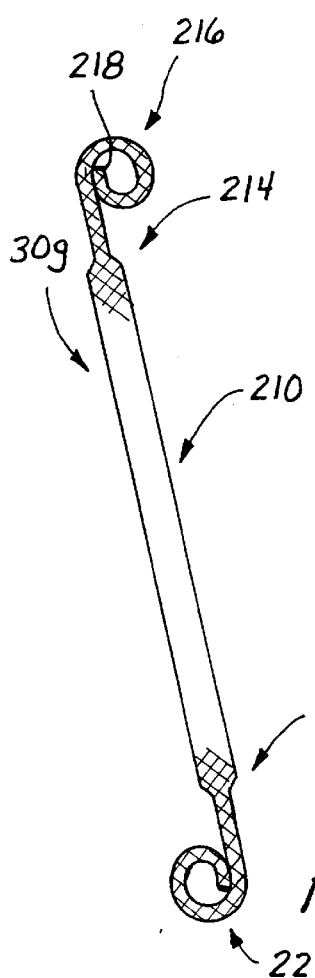

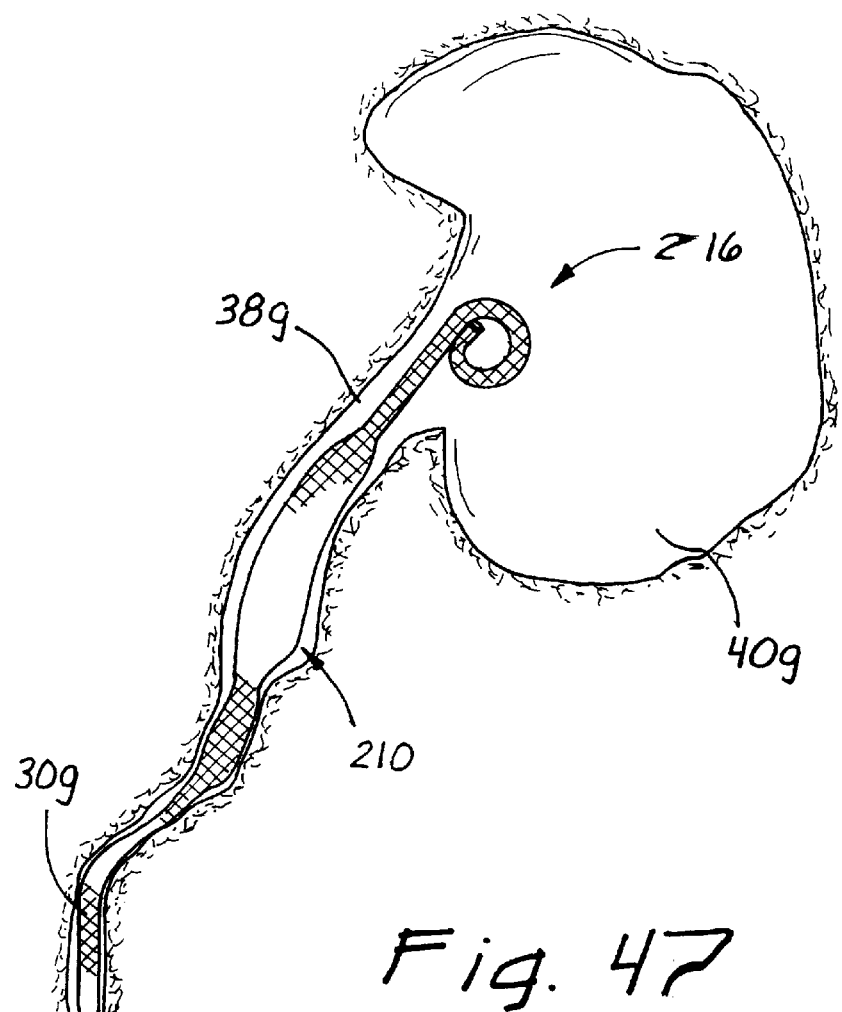
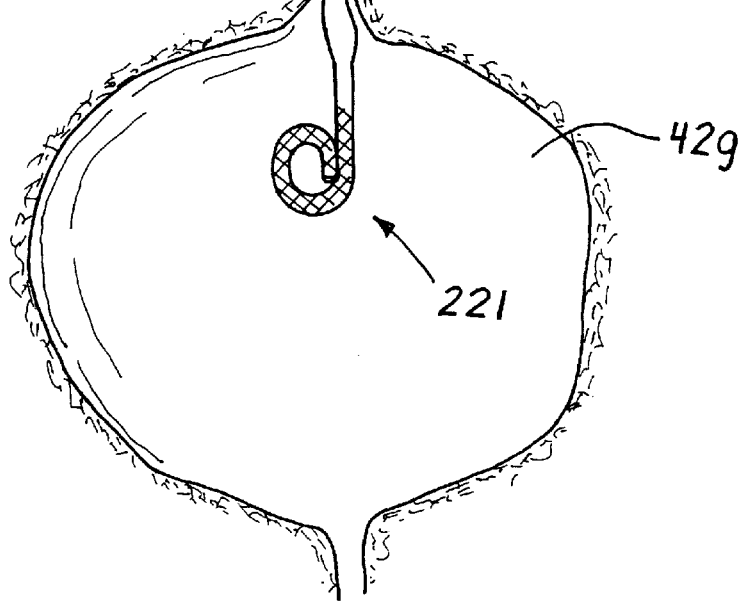
Fig. 47

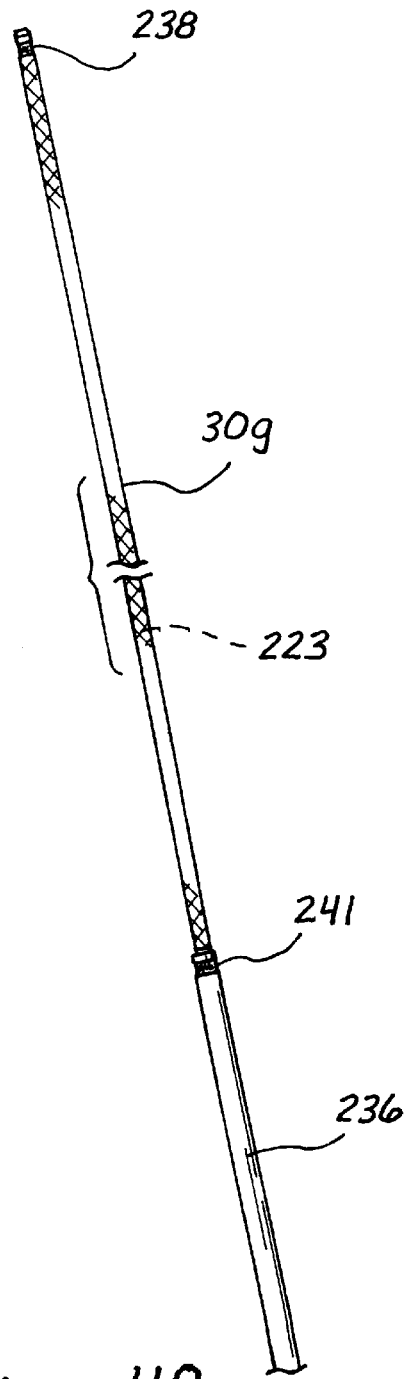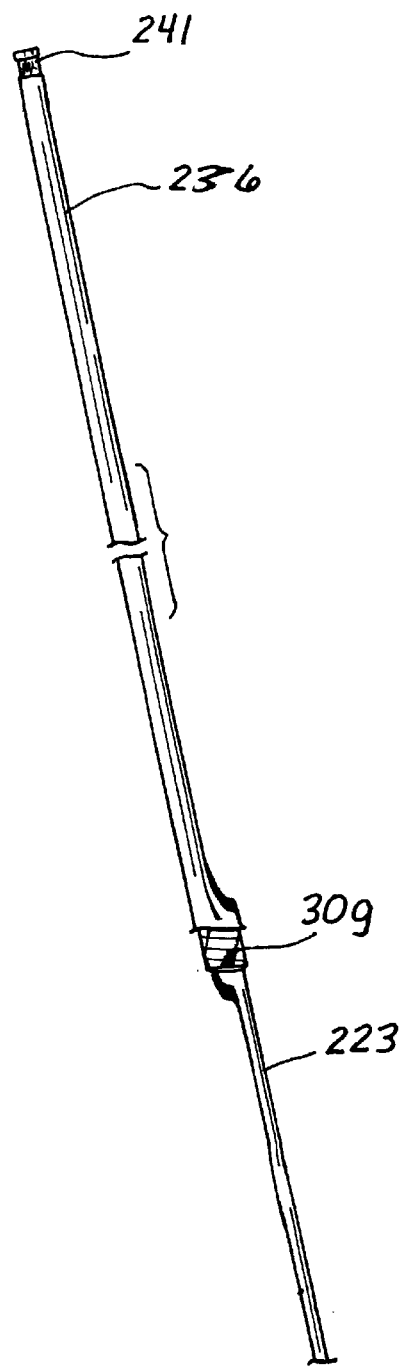

US 6,395,021 B1

URETERAL STENT SYSTEM APPARATUS AND METHOD

CROSS-REFERENCE TO RELATED APPLICATION

This application is a continuation-in-part of U.S. patent application Ser. No. 09/109,355, filed on Jul. 2, 1998, now abandoned, which is a continuation-in-part of U.S. patent application Ser. No. 08/806,337, filed on Feb. 26, 1997, both of which are incorporated herein by reference.

BACKGROUND OF THE INVENTION

1. Field of the Invention

The present invention relates generally to stents for use in supporting and maintaining an open lumen within a body passage or vessel and, more particularly, to stents configurable between large and small diameters.

2. Description of Related Art

Tubular prosthesis, which are commonly referred to as stents, are used to reinforce or strengthen body passages or vessels. Occluded, collapsed, or compromised body passages, such as blood vessels, esophagus, tracheas, gastrointestinal tracts, bile ducts, ureters, and urethras, can all benefit from stents. These body passages can become occluded, collapsed, or compromised from disease, trauma, or from specific surgical procedures upon the wall of the body passage.

Prior art stents typically comprise a length of plastic tubular material, having a number of side holes disposed along the length of the plastic tubular material. U.S. Pat. Nos. 4,913,683; 4,643,716; 5,282,784; 4,957,479; 4,931,037; and 5,364,340 describe stents generally constructed in this manner. Each of these stents has a generally fixed diameter and, therefore, is non-responsive to the specific diameter of a vessel.

A prosthesis or stent capable of expanding to appropriate diameters, along the length of the stent, can provide advantages over fixed-diameter stents. Self-expanding stents are disclosed in U.S. Pat. Nos. 5,026,377 and 5,078,720, both issued to Burton et al.; U.S. Pat. No. 5,019,085 issued to Hillstead; U.S. Pat. No. 4,969,458 issued to Wicktor; and U.S. Pat. No. 5,041,126 issued to Gianturco. These self-expanding stents are typically held in a contracted condition during insertion into the body passage or vessel and, after being positioned within the passage or vessel, released to expand fully. The stents of Wicktor and Gianturco comprise coiled or looped wires, which are unable to contact the entire surface of the interior wall of the affected vessel. The Hillstead stent incorporates a multiple-loop wire structure, which suffers from the same deficiencies associated with the Wicktor and Gianturco stents. U.S. Pat. No. 5,507,767, issued to Maeda et al., discloses a self-expanding stent that employs a plurality of straight stainless steel wire sections, separating a plurality of bends, that may be adjusted and set to fit a particular anatomy or condition. U.S. Pat. No. 5,476,505 issued to Limon discloses a coiled stent for introduction into a body passage at a first diameter and subsequent expansion within the body passage to a second diameter. This coiled stent relies on a procedure for holding a coil in a tightly-wound condition during insertion of the coiled stent. U.S. Pat. No. 5,409,019 issued to Wilk discloses a stent, which surrounds a balloon, so that the collapsed balloon, upon expansion, can expand the stent. U.S. Pat. Nos. 5,078,720 and 5,026,377 issued to Burton et al. describe a combination of a self-expanding braided stent and an instrument for deployment or retraction of the stent. The instrument for deployment or retraction of the stent includes a tubular sleeve, which surrounds and compresses the braided stent. This surrounding tubular structure requires that an additional wall thickness, corresponding to a thickness of the tubular sleeve, be added to the device during placement. Consequently, a shortcoming of the Burton et al. invention is that the placement of the device is the time when the lowest profile or smallest diameter is required.

A need remains in the prior art for a prosthesis or stent which can be placed accurately into a low-profile or small-diameter condition and which can expand in diameter to a predictable size with a predictable pressure applied to an interior surface of the vessel wall. A need also exists in the prior art for a stent having a retention feature for maintaining the stent in a preferred position within the body passage. Additionally, a need exists in the prior art for a stent having a diameter, which is capable of responding and changing to the development of the lumen of the vessel or passage.

SUMMARY OF THE INVENTION

The stent of the present invention can be introduced into a body passage or vessel in a low-profile or small-diameter and, subsequently, expanded to a large diameter. The stent can be inserted into the body passage over a guidewire or small gauge catheter in the small diameter configuration. After the guidewire or small gauge catheter is removed, the stent is transformed into the large diameter configuration, which stimulates the reactive nature of the body passage to thereby develop or maintain a patent lumen. The stent is able to provide maximum communication and flow of fluids from the surface of the stent to the other surface of the stent.

The stent of the present invention is formed of an elongate, flexible duct having a very thin wall and a pre-formed diameter, length, and shape. The stent is constructed of a woven tubular structure of multiple strands of elements. The woven tubular structure is thermally set to a predetermined diameter and length, so that the "at rest" or natural condition of the tubular structure is predictable. A retention or holding member can be formed at one or both of the ends of the stent. This retention member can be reduced in diameter or deformed or straightened for insertion into the body passage. The woven tubular structure provide a path for fluids to flow in and around the stent, while a patent lumen is being developed. The woven tubular structure allows the stent to be extended or stretched over a guidewire or other non-compressive member, to thereby reduce the diameter of the stent for insertion of the stent into a body passage.

The woven or braided stent can be formed from elements, such as polymers including polyester and metals such as Nitinol and titanium. These elements have a high-tensile strength and thereby resisting any breakage of the stent. Notwithstanding this high strength and structural integrity, the elements are generally movable relative to each other thereby providing the stent with an overall desirable, soft characteristic.

Various materials can be used to form the individual elements of the weave or braid. These materials can provide each element and the stent as a whole with considerably different characteristics at the operative site. The elements can be provided with absorbent characteristics facilitating a controlled release of drugs, chemicals, and other absorbents having medical characteristics.

In one aspect of the invention, a method of iteratively increasing a diameter of a lumen of a body passages includes the steps of inserting and moving a stent through the body passage to a desired location. At the operative site, the diameter of the stent is iteratively increased in a first iteration which provides the lumen with a first enlarged diameter and a second iteration which provides the lumen with a second enlarged diameter.

In another aspect of the invention, the stent is formed with a plurality of filaments disposed along an axis of the stent and providing the stent with an outer surface which is generally cylindrical in configuration. A material is disposed relative to the filaments which maintains the filaments in a predetermined orientation at least during insertion of the stent into a body conduit. This material may initially provide the filaments with generally rigid properties in the presence of the material and generally flexible characteristics when the material is removed.

In a further aspect of the invention, a stent is provided with a body having first characteristics advantageous during insertion of the stent and second characteristics advantageous when the stent is operatively disposed in a body conduit. A material disposed relative to the body has first properties facilitating the first characteristics of the stent body during insertion and second properties facilitating the second characteristics of the stent body when operatively disposed. The material may be bio-absorbable, and impregnated into or coated on filaments forming the body.

In still a further aspect of the invention, the stent may include a first element with first a first absorbent providing the stent with properties dependent upon the medical characteristics of the first absorbent. A second element can be included in the stent and provided a second absorbent having absorption characteristics which differ from those of the first element.

The present invention, together with additional features and advantages thereof, may best be understood by reference to the following description taken in connection with the accompanying illustrative drawings.

BRIEF DESCRIPTION OF THE DRAWINGS

FIG. 5 is a cut-away view of the stent positioned over an introducer assembly;

FIG. 6 is a cross-sectional view taken along the axis of both the stent and the introducer assembly;

FIG. 8 is a view of one embodiment of the stent of the present invention having convoluted sections at opposing ends of the stent body;

FIG. 9 is a view of one embodiment of the stent of the present invention having convolutions along the length of the stent body;

FIG. 10 is a view of a material suitable for the construction of the stent;

FIG. 11 is a view of a forming tool or mandrel being used to form the stent of the present invention;

FIG. 12 illustrates the use of a mandrel or forming tool and the use of heat to set the material of the stent to a preferred embodiment;

FIG. 13 is a view of one embodiment of the stent of the present invention having a severable mid-section;

FIG. 14 is a view of one embodiment of the stent having a tether at one end;

FIG. 22 is a side elevation view of a stent formed of filaments and provided with an impregnation or a coating in a further embodiment of the invention;

FIG. 23 is a radial cross-section view taken along lines 23—23 of FIG. 22 and illustrating an embodiment wherein the stent has a central lumen;

FIG. 24 is a radial cross-section view similar to FIG. 23 and illustrating an embodiment wherein the stent has no central lumen;

FIG. 25 is a side elevation view of an embodiment similar to that of FIG. 22 wherein the coating provides sufficient column strength to facilitate insertion of the stent;

FIG. 26 is a radial cross-section view taken along lines 26—26 of FIG. 25 and illustrating the stent to have a central lumen;

FIG. 27 is a radial cross-section view similar to FIG. 26 and illustrating the stent with no central lumen;

FIG. 28 is a side elevation view similar to FIG. 22 wherein the impregnation or coating is bio-absorbable;

FIG. 29 is a radial cross-section view taken along lines 29—29 of FIG. 28 and illustrating the stent in a low-profile state prior to insertion;

FIG. 30 is a side-elevation view similar to FIG. 28 with the coating at least partially oblated or absorbed to permit expansion of the stent to a high-profile state;

FIG. 31 is a radial cross-section view taken along lines 31—31 of FIG. 30;

FIG. 32 is a side elevation view similar to FIG. 22 wherein the filaments of the stent are disposed in a generally parallel, axial orientation;

FIG. 33 is a radial cross-section view taken along lines 33—33 of FIG. 32 and illustrating the stent to have a central lumen;

FIG. 34 is a radial cross-section view similar to FIG. 33 and illustrating a stent with no central lumen;

FIG. 35 is a side elevation view similar to FIG. 22 wherein the filaments are spiraled in a rope configuration;

FIG. 36 is a radial cross-section view taken along lines 36—36 of FIG. 35 and illustrating the stent with a central lumen;

FIG. 37 is a radial cross-section view similar to FIG. 36 and illustrating the stent with no central lumen;

FIG. 38 is a perspective view of a helical stent illustrated in a low-profile state;

FIG. 39 is a perspective view of the helical stent of FIG. 38 in a natural, high-profile state;

FIG. 40 is a perspective view of a stent having coiled ends and illustrated in a stretch configuration;

FIG. 41 is a perspective view of the coil-end stent of FIG. 40 illustrated in a natural configuration;

FIG. 42 is a side-elevation view of an additional embodiment of the invention similar to that of FIG. 41;

FIG. 43 is a side-elevation view of a positioner adapted for use with the embodiment of FIG. 42;

FIG. 44 is a side-elevation view of the stent of FIG. 42 disposed for insertion in a low-profile state on the positioner of FIG. 43;

FIGS. 45–47 illustrate steps in a preferred method for insertion of the stent of FIG. 42;

FIG. 45 is a schematic view illustrating insertion of the stent combination of FIG. 44 over a guidewire;

FIG. 46 is a schematic view illustrating the step of removing the positioner;

FIG. 47 is a schematic view of the ureter illustrating the step of removing the guidewire;

FIG. 48 is a side-elevation view illustrating the step of covering the stent and positioner combination with an oversheath;

FIG. 49 is a side-elevation view illustrating the positioner stent and oversheath in combination;

DETAILED DESCRIPTION OF THE PRESENTLY PREFERRED EMBODIMENTS

Figure 1:
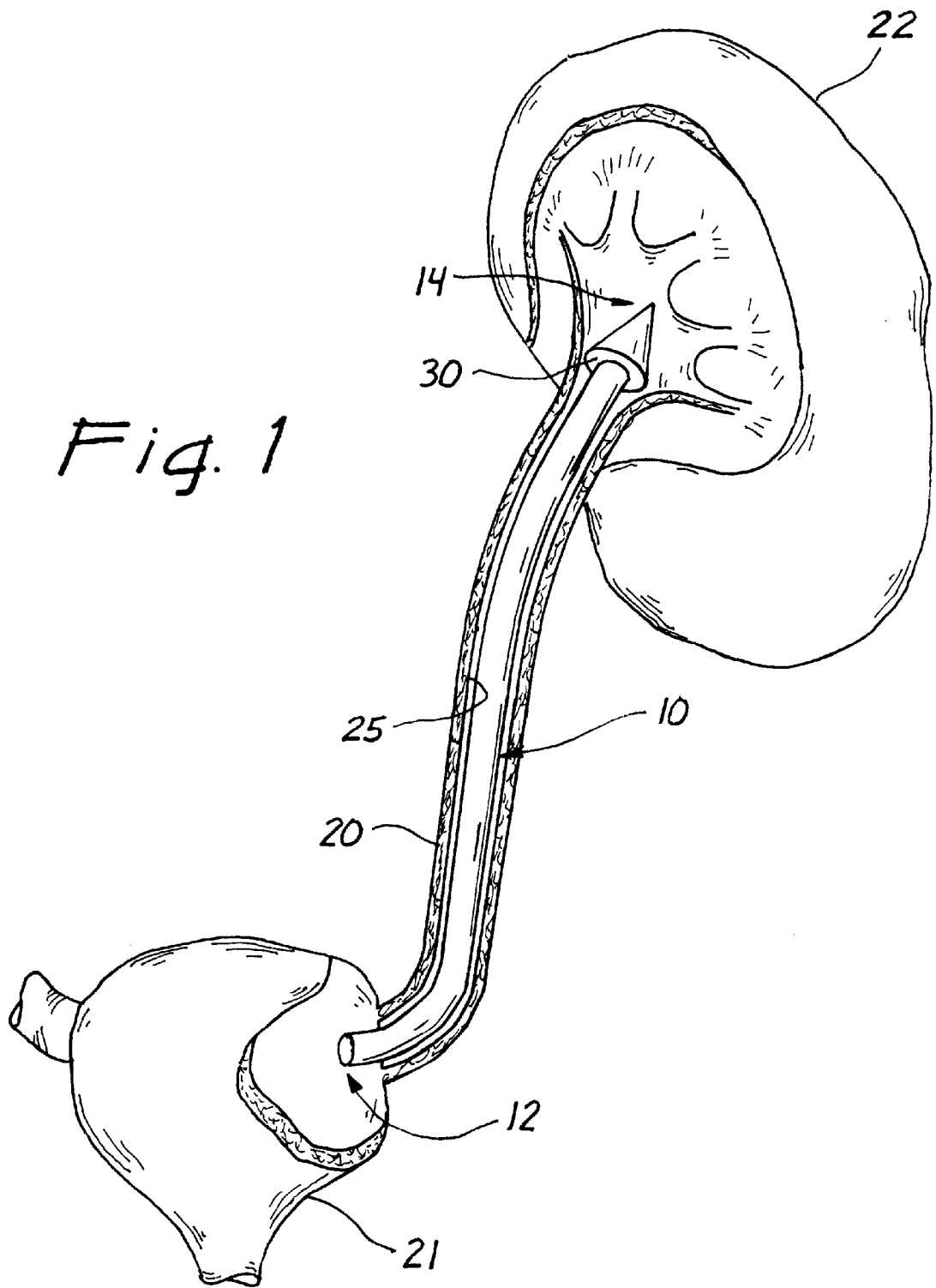
FIG. 1 is a schematic view of the stent of the present invention directed to pass through a ureter between a kidney and a urinary bladder.

Turning to FIG. 1, a stent or prosthesis 30 according to the presently preferred embodiment is illustrated having a proximal tube end 32 and a distal tube end 34. The stent body 36 is shown within a body passage or vessel 38, such as a ureter. The stent body 36 extends within the ureter 38 between a kidney 40 and a urinary bladder 42. The stent body 36 of the present invention is sized and configured to exert a compressive force against the interior surface 45 of the body passage 38. In the presently preferred embodiment, the stent 30 comprises a retention member 48 at the distal tube end 34. The stent 30 of the embodiment shown in FIG. 1 comprises a ureteral stent, which is adapted for developing or maintaining a patent lumen in the ureter 38 between the kidney 40 and the urinary bladder 42. The stent 30 facilitates passage of fluid in, through, and around the stent body 36 from the kidney 40 to the urinary bladder 42.

Figure 2:
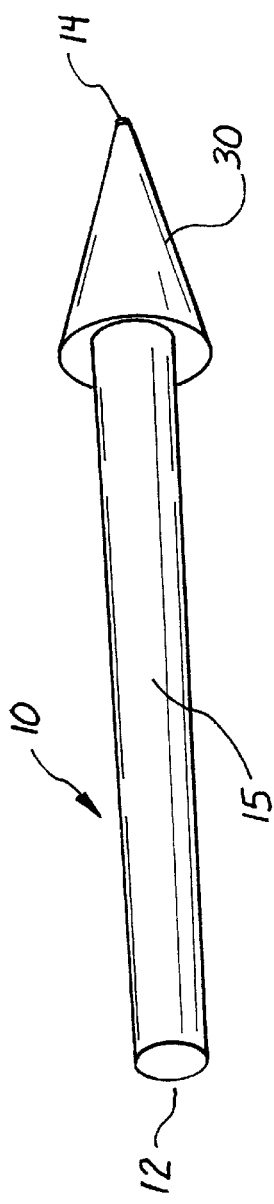
FIG. 2 is a side view of the stent in a radially expanded condition.

The stent of the present invention preferably comprises a woven material, which can be elongated and contracted. FIG. 2 is a side view of the stent 30 in a contracted, radially expanded condition. The condition illustrated in FIG. 2 corresponds to an "at rest" or natural condition of the stent 30. The lumen of the stent body 36 is fully developed along the length of the stent body 36, narrowing only at the distal tube end 34. The retention member 48, which forms a cuff or enlargement sized and configured to engage a portion of an organ or passage, has an enlarged diameter in the natural condition shown in FIG. 2. The retention member 48 assists in maintaining the stent 30 within the body passage 38, as illustrated in FIG. 1, for example.

Figure 3:
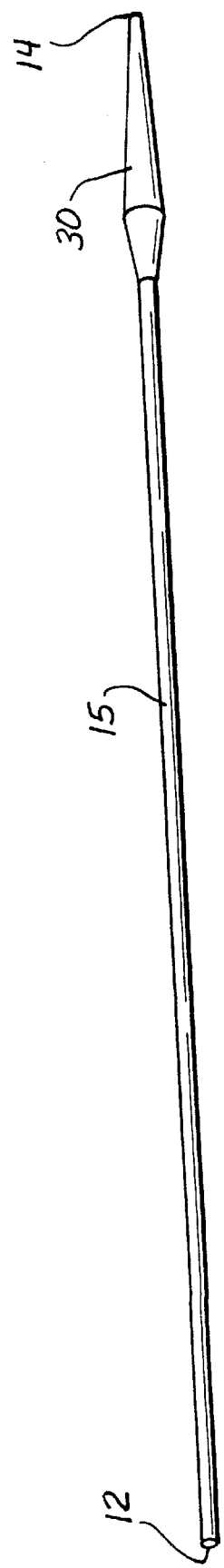
FIG. 3 is a side view of the stent in a radially compressed and longitudinally extended condition.

FIG. 3 illustrates the stent 30 in a stretched, radially compressed and longitudinally extended condition. The stent body 36 is preferably reduced in diameter in order to facilitate placement of the stent 30 into a body passage 38. When the stent 30 is stretched along its axis, the diameters of the stent body 36 and the retention member 48 are significantly reduced to facilitate a low-profile configuration for insertion into the body passage 38. As presently embodied, the stent 30 is placed into the low-profile condition by application of a tensile force applied to both the proximal tube end 32 and the distal tube end 34.

Figure 4:
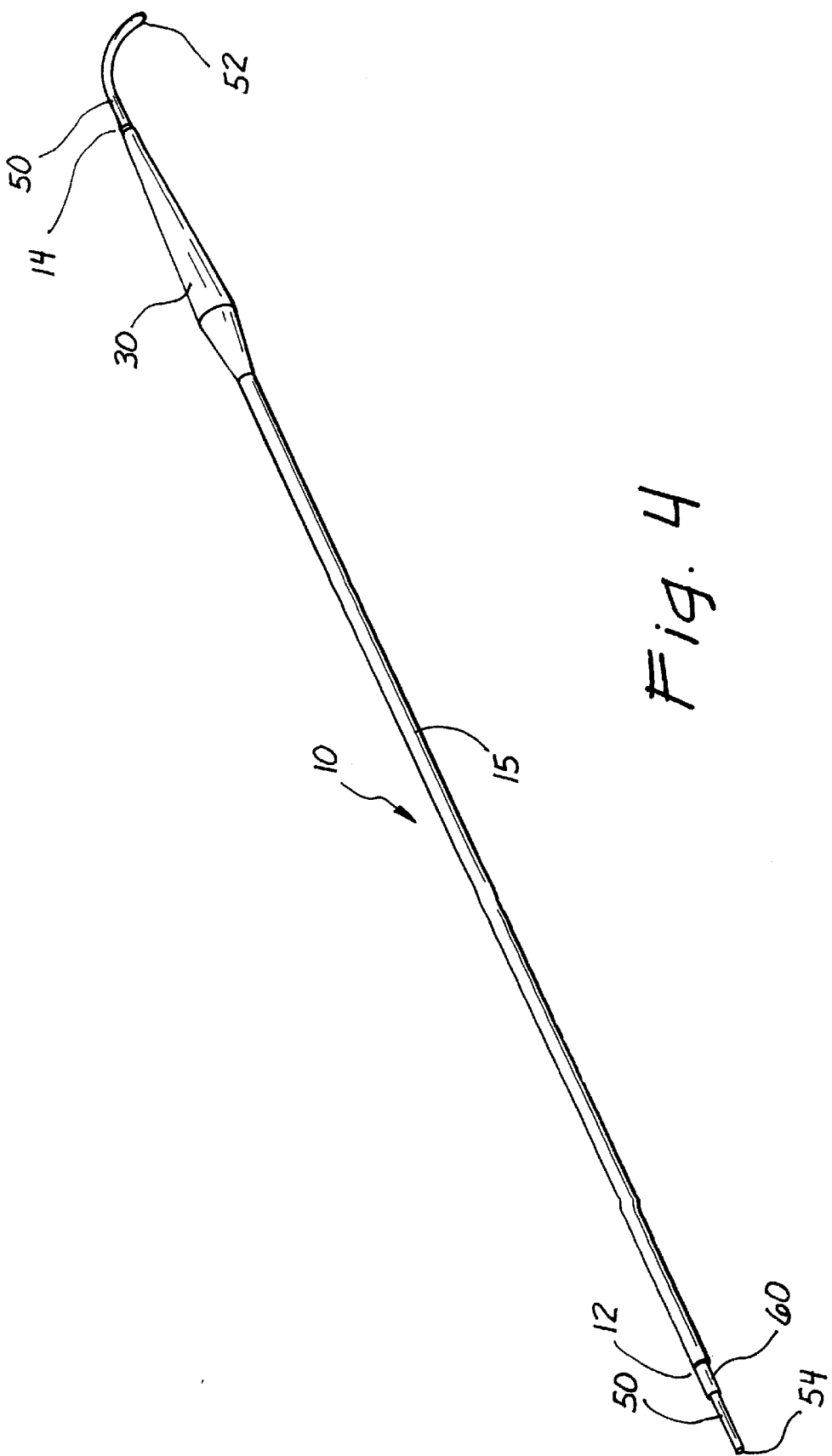
FIG. 4 is a side view of the stent of the present invention showing an introducer assembly.

As illustrated in FIG. 4, a compression sleeve 60, having a proximal end 62 and a distal end 64 (FIG. 5), can be inserted into a lumen of the stent 30. The compression sleeve 60 is preferably inserted into the lumen of the stent 30, until the distal end 64 of the compression sleeve 60 contacts the distal tube end 34 of the stent 30. After this placement, the proximal tube end 32 of the stent 30 can be drawn proximally, relative to the compression sleeve 60, to thereby facilitate elongation of the stent 30. In other words, since the distal end of the compression sleeve 60 cannot pass through the narrow aperture of the distal tube end 34, movement of the proximal tube end 32 proximally will lengthen the stent 30. As the stent 30 increases in length, the diameter of the stent 30 decreases. The reduced diameter of the stent 30 facilitates a less-intrusive insertion of the assembly into a body passage 38.

A guidewire 70, having a proximal end 72 and a distal end 74, may be placed within the compression sleeve 60. The guidewire 70 provides a means for establishing a track, so that the stent 30 and compression sleeve 60 may be advanced along the guidewire 70 to a desired location within the body passage 38, with the stent 30 in an elongated configuration. After the stent 30 is moved to the desired location, the proximal tube end 32 of the stent 30 is released or relaxed, to thereby allow the proximal tube end 32 to move distally, resulting in an enlargement of the diameter of the stent 30. According to the presently preferred method of insertion, the guidewire 70 is placed within the body passage 38, and the stent 30 is then placed over the proximal end 72 of the guidewire 70. Next, the compression sleeve 60 is placed over the proximal end 72 of the guidewire 70 and into the stent body 36.

FIG. 5 illustrates a cut-away view of the stent 30 positioned over both the compression sleeve 60 and the guidewire 70, and FIG. 6 illustrates a cross-sectional view of the assembly shown in FIG. 5. As illustrated in FIGS. 5 and 6, the compression sleeve 60 fits between the stent 30 and the guidewire 70. The opening at the distal end 34 of the stent 30 does not permit the distal end 64 of the compression sleeve 60 to pass through. This configuration permits the stent 30 to be stretched lengthwise, as the proximal end 32 of the stent 30 is extended proximally along the surface of the compression sleeve 60. At full extension, the profile of the stent 30 exceeds the outside diameter of the compression sleeve 60 by the thickness of the wall of the stent body 36. This extended/compressed relationship exists as long as a holding force is maintained between the proximal end 32 of the stent 30 and the compression sleeve 60. When this force is removed, the stent 30 assumes an "at rest" or expanded profile.

Figure 7:
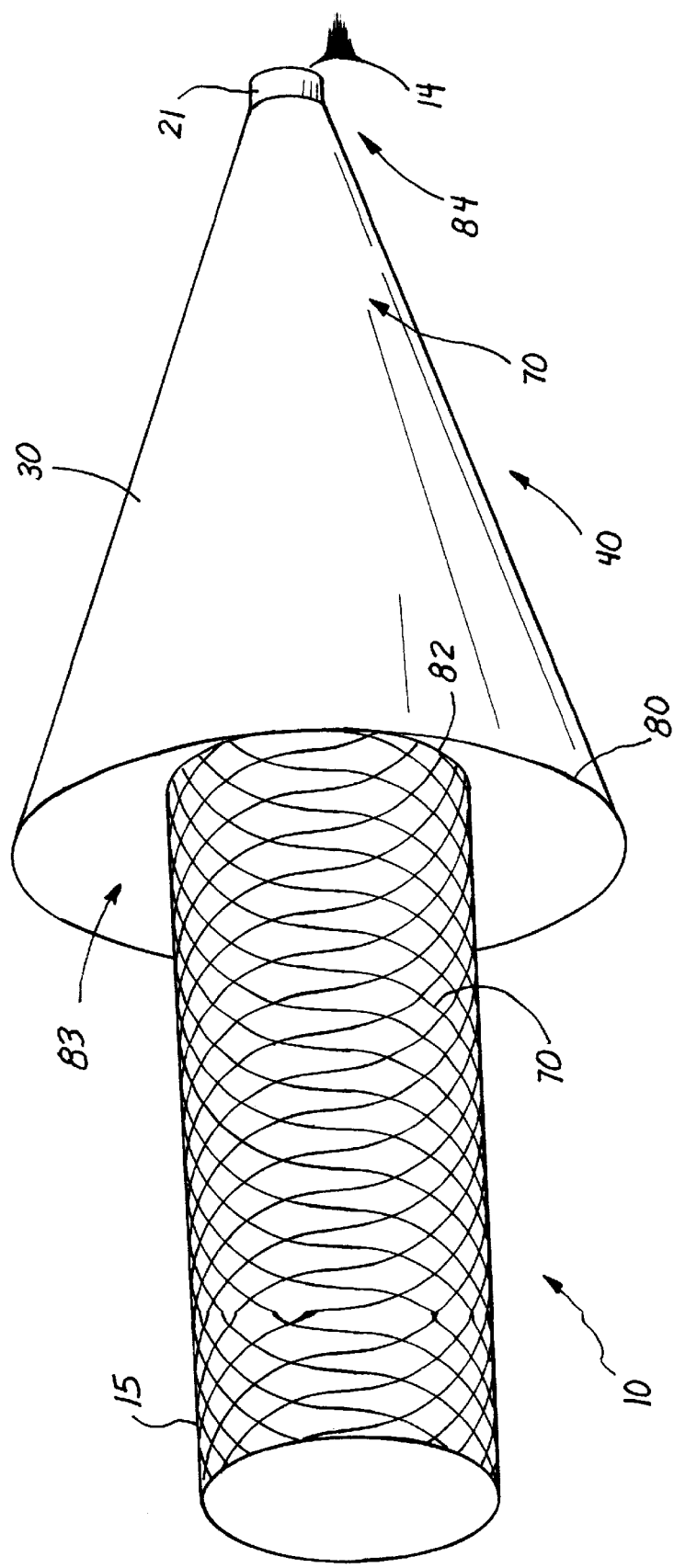
FIG. 7 is an enlarged view of the retention member of the stent according to the present invention.

FIG. 7 illustrates an enlarged view of the retention member 48 of the presently preferred embodiment. The retention member 48 preferably comprises an enlarged diameter capable of engaging a portion within a vessel or organ, to thereby prevent the stent 30 from migrating or slipping from a desired position or location within the vessel or organ. The distal ring 81 of the retention member 48 is preferably sized and configured to prevent the compression sleeve 60 (FIG. 5) from passing therethrough. The distal ring 81 preferably comprises a thermally fused or melted portion of material fibers 84 from which the stent 30 is woven. The distal ring 81, however, may be formed in other ways and/or comprise other materials. In the presently preferred embodiment, the retention member 48 comprises the shape of a cone 87 having a small diameter portion 89 distally located from a large diameter portion 92. The retention member 48 preferably comprises a substantially folded lip section 95 and a substantially folded angular portion 98 providing a transition between the stent body 36 and the retention member 48.

FIGS. 8 and 9 illustrate stents 30 having series of convolutions 100, 102, and 104 formed along the stent bodies 48. These convolutions 100, 102, 104 can operate to add strength to the retention members 48 and 107. The convolutions 100, 102, 104 also provide additional strength to the stent bodies 36 for resisting compression in much the same way as corrugated tubing resists kinking and compression. Additionally, the convolutions 100, 102, 104 assist in providing traction within the lumen of a body passage 38 and are sized and configured to be reduced in profile in the same manner as the stent body 36 by the application of traction or tension upon the stent body 36.

As illustrated in FIG. 10, the stent 30 is formed from an initial woven tubular structure 111, which preferably comprises a thermoplastic material or mesh. This construction begins by weaving or braiding a plurality of individual or groups of individual fibers or elements 84 into a tubular stent body 36. Desired characteristics may be developed within this construction for providing ratios of expansion to extension, as is known in the art.

After the woven tubular structure 111 is generated, the woven tubular structure 111 is placed onto a forming tool or mandrel 113 having a proximal end 115 and a distal end 117. The mandrel 113 serves as a form in setting the thermoplastic material of the woven tubular structure 111. In the presently preferred embodiment, the forming tool 113 comprises a first diameter near the proximal end 115 and a second diameter near the distal end 117. The first diameter represents the desired maximum deployed or expanded diameter of the stent body 36 when the stent body 36 is within a body passage or vessel 38, and the second diameter corresponds to the diameter of a conventional guidewire 70 (FIG. 6) but compression sleeve 60 (FIG. 6).

Alternatively, the stent 30 can be formed of metal material such as Nitinol (a trademark of Raychem, Inc.) or a titanium. Nitinol is well-known for its heatset properties which would enable it to function in the manner previously discussed. Titanium has excellent bio-compatibility features which might make it a preferred material in a particular environment.

The woven tubular structure 111 of the stent 30 is folded proximally upon the forming tool 113 to thereby form the retention member 48. As shown in FIG. 12, the forming tool 113 and the woven tubular structure 111 are next exposed to radiation 121 from a heat source or an oven preferably at a temperature sufficient to set the material of the woven tubular structure 111 to the preferred condition. In the presently preferred embodiment, the material comprises a thermoplastic, such as a polyester or nylon, since these materials allow for the development of a permanent, thermally-set condition. Additionally, the distal tube end 34 and the distal ring 81 are preferably fused or melted to form a solid ring or collar which provides support for the compression sleeve 60. As a secondary operation, a proximal portion 123 of the stent body 36 may be coated with an elastomeric material to thereby provide stability at the proximal portion 123.

FIG. 13 illustrates a stent 30 having a tether 130 attached or formed at the proximal tube end 32 for assisting in the placement or the removal of the stent 30 from a body passage 38.

FIG. 14 illustrates a stent having a first retention member 48 and a second retention member 136 located at an end opposite from the first retention member 48. The stent having the two retention members 48, 136 may be used as is or, alternatively, the stent may be cut at a preferred location 138 to form two individual stents 140 and 142.

Figure 15:
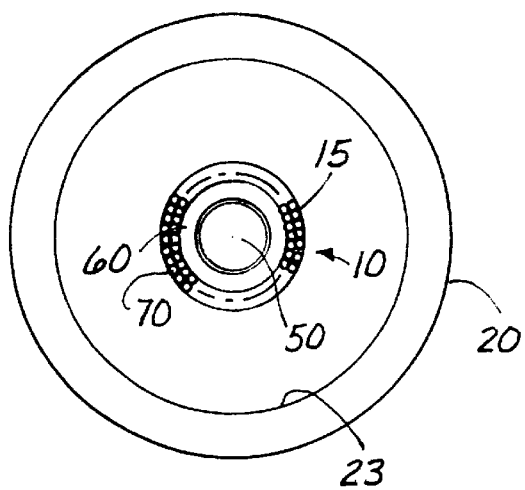
FIG. 15 is an end view of the stent in an elongated condition within a body passage or vessel.
Figure 16:
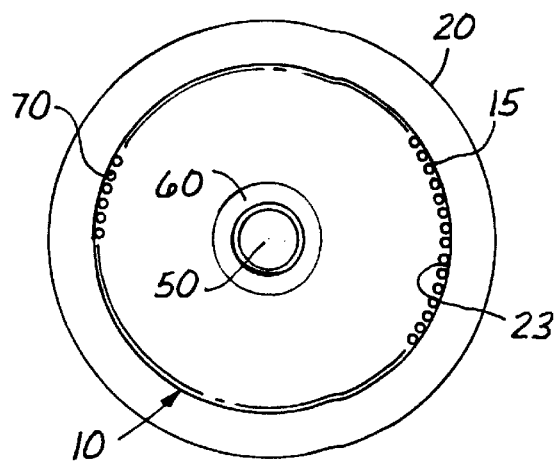
FIG. 16 is an end view of the stent in an expanded condition within a body passage or vessel.
Figure 17:
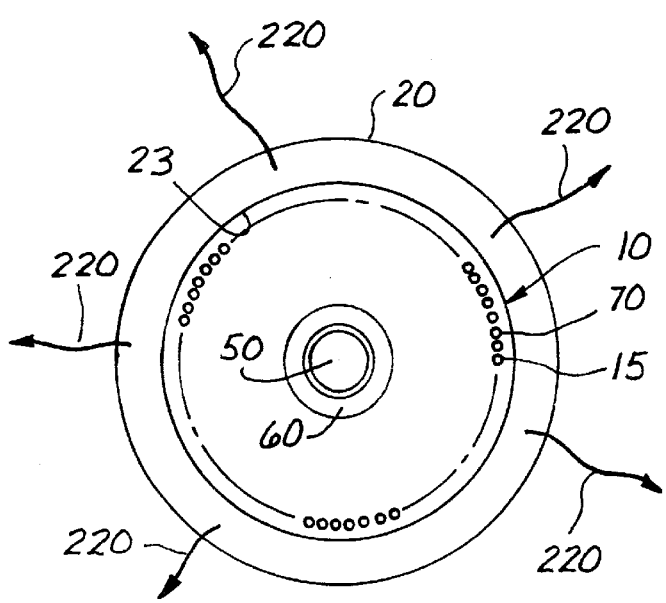
FIG. 17 is an illustration of the forces applied outwardly from the axis of the stent and against the wall structure of the body passage or vessel.

FIG. 15 illustrates an end view of the stent 30 of the presently preferred embodiment within a body passage 38. The stent 30 is illustrated in an extended, small diameter condition over both the compression sleeve 60 and the guidewire 70. FIGS. 16 and 17 illustrate the stent 30 in a large-diameter relaxed state. The guidewire 70 and the compression sleeve 60 may be removed at this time. The stent body 36 exerts a constant outward pressure 151 upon the interior surface 45 of the body passage 38. This outwardly directed radial pressure, along with the naturally occurring tendency for the intimal tissue to move away from a foreign body, combines to enlarge and/or maintain the lumen of the body passage 20.

Figure 18:
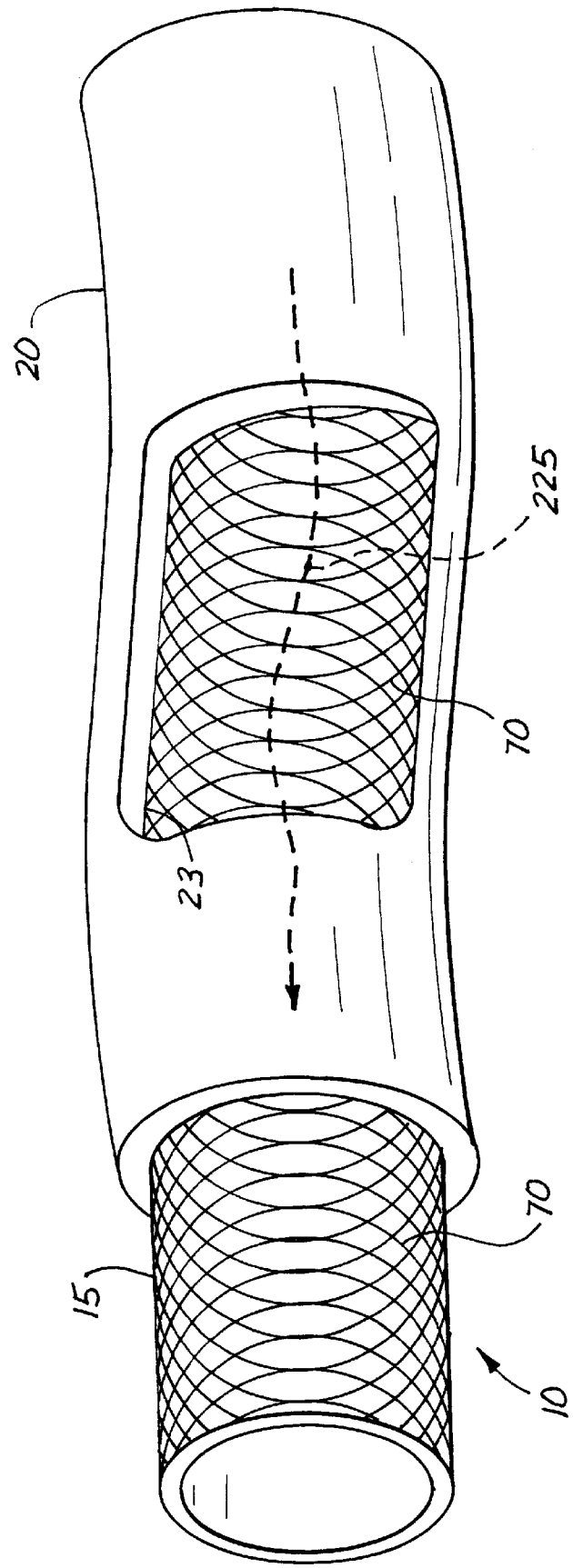
FIG. 18 is a cut-away view of the stent within a body passage or vessel in an expanded condition.

An enlarged view of a body passage 38 is provided in FIG. 18 with a stent 30 of the presently preferred embodiment fully extended within the lumen of the body passage 38. The individual fibers or groups of fibers 84 are spaced apart to thereby allow for the flow 155 of fluid through and around the stent body 36 as the stent body 36 applies outward pressure to the interior surface 45 of the body passage 38.

Figure 19:
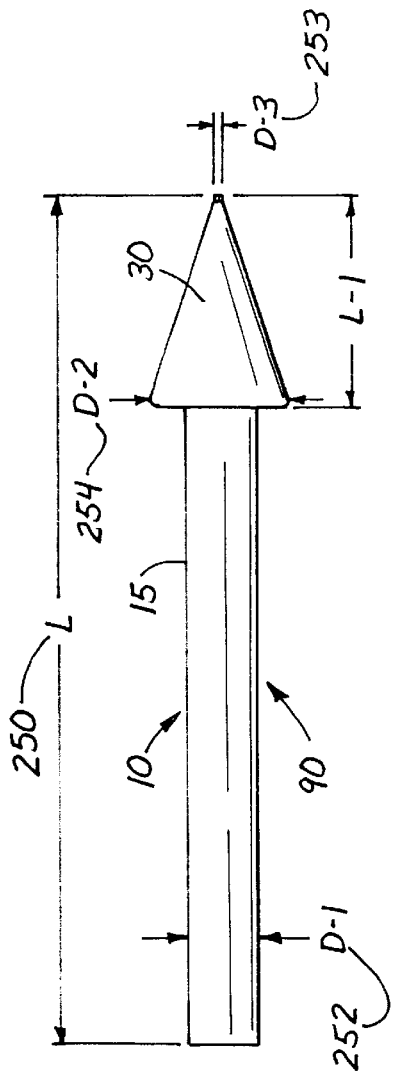
FIG. 19 illustrates the relative length to diameter feature in an expanded condition of the stent.
Figure 20:
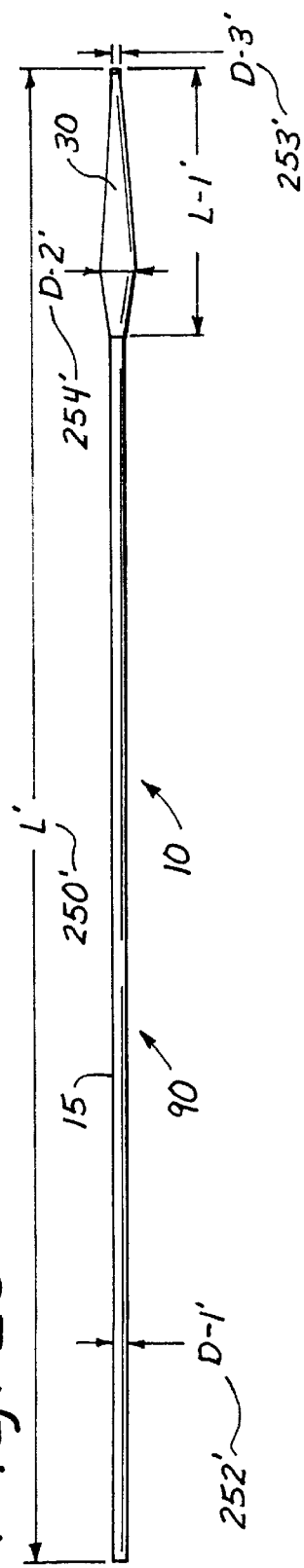
FIG. 20 illustrates the relative length to diameter feature in an extended condition of the stent.
Figure 21:
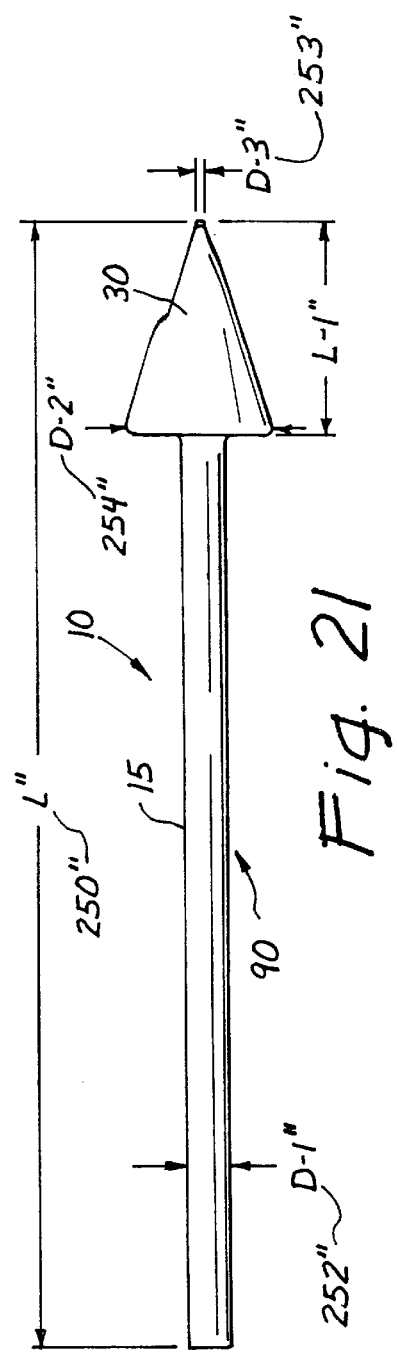
FIG. 21 illustrates the relative length to diameter feature in an intermediate condition of the stent.

The relationship between the length and the diameter of the stent 30 of the present invention is illustrated in FIGS. 19–21. The stent 30 in the "at rest" or natural, relaxed condition is illustrated in FIG. 19 with a fully expanded, maximum diameter 172. Due to the naturally occurring relationship of the fibers or elements 84 of a woven or braided tubular structure 111 (FIG. 10), a change in length 170 will accompany any change in diameter 172. Conversely, any change in length 170 precipitates a commensurate change in diameter 172. The present invention harnesses this relationship to facilitate the placement, maintenance, and removal of the stent 30. As presently embodied, the length 174 and the diameter 176 of the retention member 48 change somewhat proportionally to changes in the length 170 and diameter 172 of the stent body 36.

With reference to FIG. 20, as the stent 30 is stretched or extended in length 180, 181, the diameters 182 of the stent body 36 and the diameter 186 of the retention member 48 are both reduced. Upon removal or relaxation of the stretching or extending force, the stent 30 attempts to assume an original "thermally set" or natural condition within the body passage. Accordingly, the length 190 and the diameter 192 increase from the length 180 and the diameter 182 of FIG. 20, as illustrated in FIG. 21. Similarly, the length 191 and the diameter 196 of the retention member 48 increase. The increased diameters 192, 196 exert radially outwardly directed forces upon any resistive structure. As the diameters 192, 196 increase, the lumen within the body passage 38 will also increase, thereby facilitating further increases in the diameters 192, 196.

The intimal tissue of the body passage 38 responds to the presence of the braided material by moving away from the stent 30. Thus, the lumen of the body passage 38 enlarges in response to the presence of the stent 30. As the lumen enlarges, the self-expanding stent 30 follows the inner surface of the body passage 38 and continues to expand. This, in turn, stimulates further enlargement of the lumen of the body passage 38. This expansion-response of the stent 30 and body passage 38 continues until a maximum lumen diameter is achieved.

The expansion-response reaction of the body passage 38 is believed to be a reaction to the members of the braided material and the motion of these members within the body passage 38, especially when the body passage comprises a ureter. The expansion-response reaction may also be attributed generally to a foreign body reaction within the body passage 38. In the particular case of a ureter, it is believed that the irritation from the braided or woven members causes this response.

A further embodiment of the invention is illustrated in FIG. 22 wherein elements of similar structure are designated by the same reference numeral followed by the lower case letter "a." Thus, stent 30a includes a plurality of fibers or filaments 84a which extend generally along an axis 200 between proximal end 32a and distal end 34a.

The filaments 84a may be oriented to provide the stent 30a with a central lumen 203, best illustrated in FIG. 23. Alternatively, the stent 30a may be formed with a generally solid configuration, free of any central lumen, as illustrated in FIG. 24. In combination these filaments 84a provide the stent 30a with a generally cylindrical outer surface 202. In the embodiment of FIG. 22, the stent 30a is also provided with a material 204 which at least partially impregnates and/or coats the filaments 84a.

The filaments 84a, together with the material 204, can provide the stent 30a with a variety of characteristics. For example, in FIG. 22, the filaments 84a have a generally rigid configuration when coated or impregnated with the material 204. However, in the absence of the material 204, the filaments 84a may be more limp and flexible. Taking advantage of these characteristics of the filaments 84a, the material 204 can be chosen with bio-absorbable characteristics. When the material 204 is disposed relative to the filaments 84a, the stent 30a has the generally rigid characteristics which facilitate its insertion into the body passage or conduit. However, once the stent 30a is operatively disposed within the conduit, the material 204 is at least partially absorbed or otherwise removed, leaving the stent 30a with the generally flexible characteristics and thereby facilitating the fluid-flow properties of the stent.

In the embodiment of FIG. 25, elements of similar structure are designated by the same reference numerals followed by the lower case letter "b." In this case, the material 204b is coated on, impregnated into, or otherwise disposed relative to the filaments 84b. As illustrated in FIGS. 26 and 27, the stent 30b may be provided with a central lumen 203b or, alternatively, provided with a generally solid structure, respectively. The material 204b is of particular interest in this embodiment as it is chosen to provide the stent 30b with a generally fixed, predetermined length and diameter. Nevertheless, the material 204b may be very flexible. In this case, the stent facilitates fluid flow between its ends 32b and 34b in a "wicking" action.

Another embodiment is illustrated in FIG. 28 wherein like elements of structure are designated by the same reference numeral followed by the lower case letter "c." In this case, the characteristics chosen for the filaments 84c and the material 204c are of particular interest. For example, the filaments 84c can be made from a material having expansion characteristics which cause the stent 30c to automatically move from a low-profile state to a high-profile state. The material 204c can be chosen with bio-absorbable characteristics whereby the stent 30c is maintained in its low-profile state in the presence of the material 204c, as illustrated in FIG. 28. In this low-profile state, the stent 30c may have a generally solid configuration as illustrated in the radial cross-section view of FIG. 29.

In this embodiment, it is the properties of the material 204c which initially hold the filaments 84c in the low-profile state. However, after the stent 30c is inserted into the body conduit, these bio-absorbable characteristics cause the material 204c to be absorbed, ablated, or otherwise at least partially removed from the filaments 84c. This permits the filaments 84c to expand to the high-profile state as illustrated in FIG. 30. In this view, and the radial cross-section view of FIG. 31, a dotted line 206 illustrates the material 204c in a partially removed state permitting automatic expansion of the filaments 84c. In this embodiment, the bio-absorbable material 204 includes polyglycolic acid.

It can be seen that in several of these embodiments, it is the combination of characteristics present in the filaments 84 and the material 204 which are relied on to provide the stent 10 with different properties facilitating insertion on the one hand and operative disposition on the other hand. For example, in the embodiment of FIG. 28, the filaments 84c have first characteristics, such as a low-profile, and second characteristics, such as a high-profile. Similarly, the material 204 has first characteristics, such as an integrous coating on the outer surface 202c, and second characteristics, such as a weakened or absorbable coating. In combination, the first characteristics of the material 204 facilitates the first characteristics of the filaments 84 while inhibiting the second characteristics of the filaments 84. This facilitates insertion of the stent 10. When the stent 10 is operatively disposed, the second characteristics of the material 204 facilitate the second characteristics of the filaments 84 while inhibiting the first characteristics of the filaments 84. This provides the stent 30c with the best performance when disposed at the operative site.

The embodiments of FIGS. 32, 35, and 38 include elements similar to those previously discussed which are designated by the same reference numerals followed by the lower case letters "d", "e", and "f", respectively. These embodiments are illustrative of the fact that the filaments 84 can be disposed in any relative configuration typically providing the stent 10 with an elongate, cylindrical configuration. For example, the filaments 84c in FIG. 28 may be woven whereas the filaments 84d in FIG. 32 are generally straight and parallel to the axis 200d. These filaments 84d can be oriented to provide the stent 10d with a central lumen 203d as illustrated in FIG. 33, or a generally solid configuration as illustrated in FIG. 34. In this embodiment, the material 204d is shown to be impregnated into the filaments 84d.

In a further orientation, illustrated in FIG. 35, the filaments 84e are spiraled in a rope configuration. This embodiment may also be formed with a central lumen 203e as illustrated in FIG. 36, or a generally solid configuration as illustrated in FIG. 37.

A further embodiment providing a spiraled configuration is illustrated in FIG. 8 wherein the stent 30f is formed as a helix or spring. With this configuration, the stent 30f may have a single element 84f or a polarity of elements each forming a helical spring. Where multiple springs are contemplated, the elements 84f may be disposed one within the other and may also be spiraled in different directions.

In FIG. 38, the stent 30f is illustrated in a low-profile state which is achieved by separating the ends 32f and 34f. This low-profile state facilitates insertion of the stent 30f. When the ends 32f and 34f are released, the helix is free to return to its normal high-profile state, as illustrated in FIG. 39. In this embodiment, the desired freedom of movement of the filament 84f between its ends 32f and 34f is facilitated by the convolutions of the helical spring which are free to move relative to each other. Coils 205 and 206 can be formed at the ends 32f and 34f as illustrated in FIG. 39. These coils 205, 206, which automatically form when the stent 30f is in its natural state, tend to anchor the stent 30f in its operative position. Of course, when the stent 30f is initially inserted, it is desirable that these coils 205 and 206 straighten along the axis of the stent as illustrated in FIG. 38. In this stretched configuration, the stent 30f can be easily inserted into the conduit and then released to form its untensioned, natural state as illustrated in FIG. 39.

These same coils 205 and 206 can be formed in the embodiment illustrated in FIGS. 40 and 41 wherein similar elements are designated by the same reference numerals followed by the lower-case letter "g". In this embodiment, the stent 30g is formed from braided or woven elements 84g which extend between the stent ends 32g and 34g. In this embodiment, the coils 205g and 206g can be formed in the ends of the stent 30g as previously discussed. These coils 205g and 206g can be axially oriented by tensioning the stent 30g as illustrated in FIG. 40. This facilitates insertion of the stent 30g which returns to its natural state as illustrated in FIG. 41 when tension is removed at the operative site.

The stent 30g is further illustrated in FIG. 42 to include a body portion 210 with a proximal end 212 and a distal end 214. This body portion 210 has a tubular configuration with a diameter such as one-eighth inch to one-quarter inch. Extending from the distal end 214, an anchor portion 216 can be provided in a contiguous relationship with the body portion 210. This anchor portion 216 also has a tubular configuration and is connected at one of its ends to the distal end 214 and is provided at its other end with a constriction 218. The anchor portion 216 may also have a tubular configuration and may be formed as an extension of the mesh defining the body portion 210. A similar anchor portion 221 can be coupled to the proximal end 212, but it is preferably formed without a constriction.

As in previous embodiments, the filaments forming the mesh of the stent 30g can be heatset so that, at rest, the stent 30g tends toward the general shape illustrated in FIG. 42. This shape includes the enlarged body portion 210, as well as the pigtail configuration of the anchor portions 216 and 221. With these heatset properties, the stent 30g is particularly adapted for insertion using a positioner 223 such as that illustrated in FIG. 43. This positioner 223 preferably has the configuration of a tube with an interior lumen 225. The positioner 223 can be formed of flexible or semi-rigid material, and provided with a generally straight, but bendable, configuration.

In operation, the positioner 223 is inserted into the anchor portion 221 at the proximal end of the stent 30g. It is moved through the stent 30g until it abuts the constriction 218 at the end of the anchor portion 216, as illustrated in FIG. 44. In this configuration, the stent 30g is maintained in a generally straight configuration and stretched to a low-profile state facilitating insertion.

Figure 45:
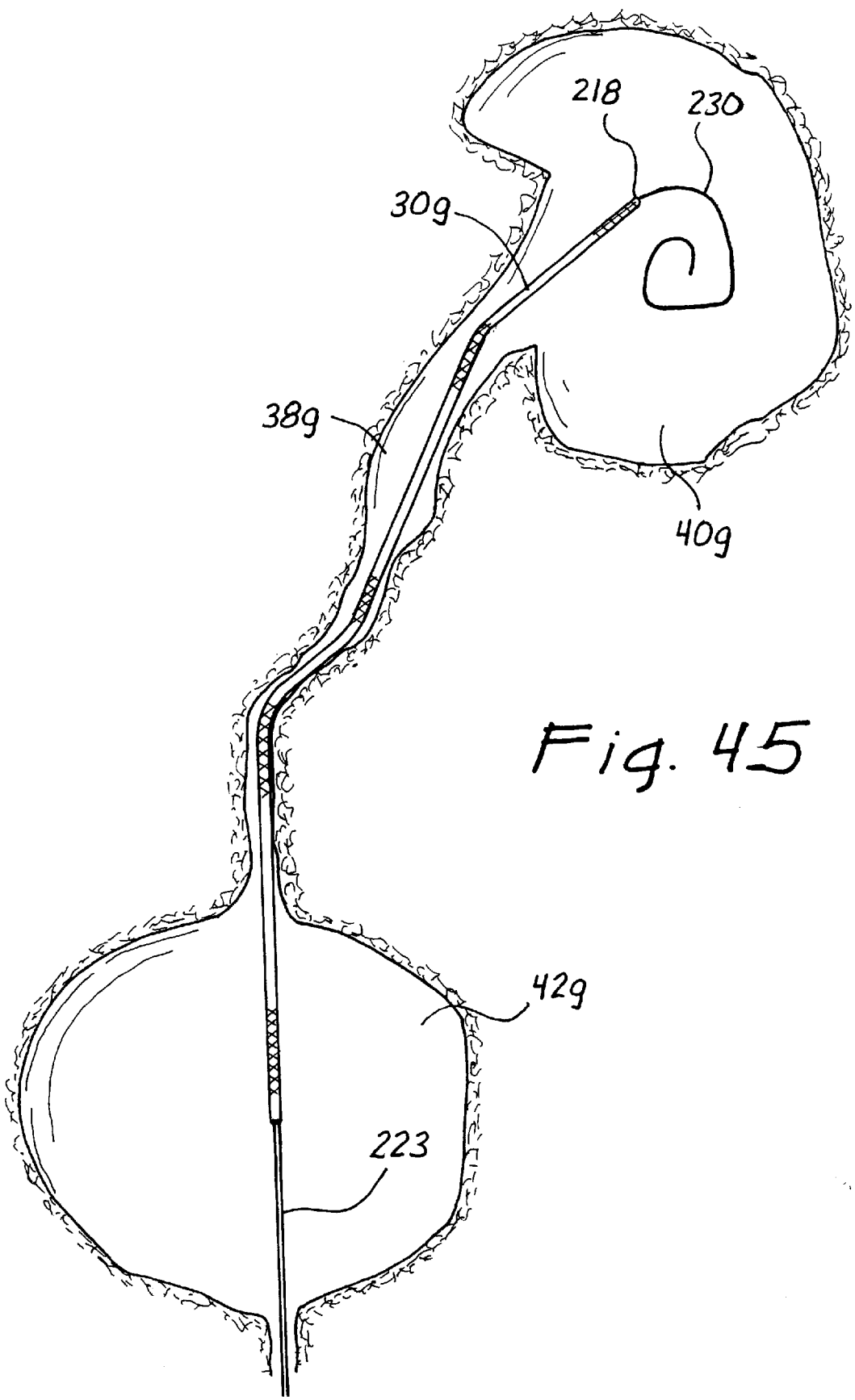

Operative disposition of the stent 30g is best described with reference to FIGS. 45–47. In these figures, the ureter 38g is illustrated between the bladder 42g and the kidney 40g. Initially, a guidewire 230 can be introduced through the bladder 42g and into the kidney 40g. With the positioner 223 operatively disposed in the stent 30g, as illustrated in FIG. 44, this combination can be introduced over the guidewire 230g, as illustrated in FIG. 45. In accordance with this method, the guidewire tends to guide the positioner 223 and stent 30g through the tortuous path of the ureter 38g.

Figure 46:
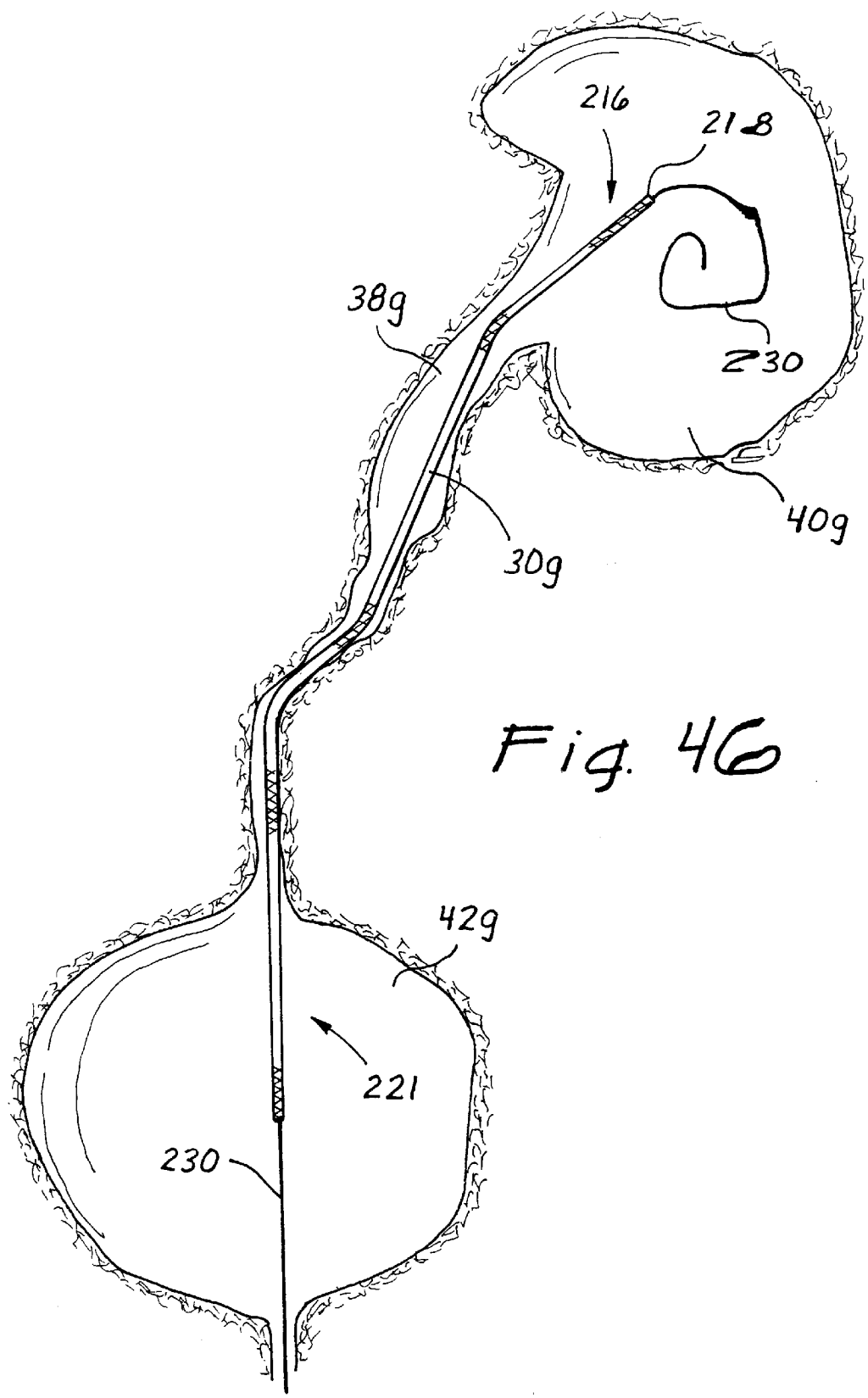

Once the stent 30g is appropriately positioned with the body portion 210 disposed in the ureter 30g, the positioner 223 can be withdrawn leaving the stent 30g and the guidewire 230, as illustrated in FIG. 46. The guidewire 230 can then be moved from the stent 30g leaving the stent 30g operatively disposed with the body portion 210 in the ureter 38g, the anchor portion 216 in the kidney 40g, and the anchor portion 221 in the bladder 42g. In the absence of either the positioner 223, or the guidewire 230, the heatset characteristics will cause the ends of the stent 30g to curl or coil into a pigtail configuration, as illustrated in FIG. 47. These same heatset characteristics will cause the body portion 210 of the stent 30g to expand, thereby irritating the walls of the ureter 38g and causing them to further expand the diameter of the ureter 38g.

As illustrated in FIG. 48, a second pusher 235 can be provided to abut the proximal end of the stent which is mounted on the first positioner 223. The second positioner 235 can aid in releasing the stent 30g from the first positioner 223 as it is withdrawn through the stent.

An oversheath 236, but illustrated in FIG. 49, can be provided to cover the combination of the positioner 223 and stent 30g. When operatively disposed, the oversheath 236 covers at least a portion of the stent 30g, as illustrated in FIG. 49. The placement of radiopaque markers 238 and 241 on the stent 30g and sheath 236, respectively, can facilitate maintenance of this operative disposition. When the oversheath 236 is in place, the mesh configuration of the stent 30g is replaced with a smooth outer surface of the oversheath 236 to facilitate introduction of the stent into the ureter 38g.

Figure 50:
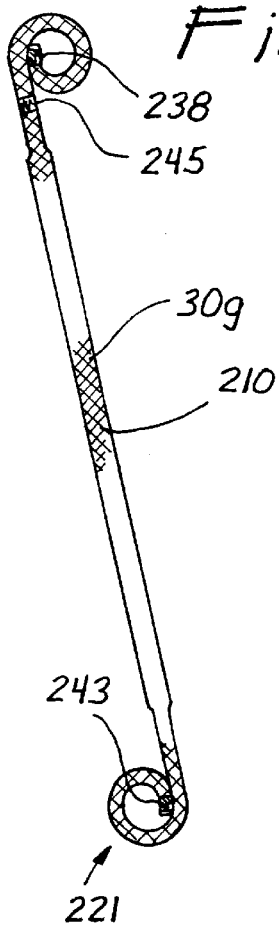
FIG. 50 is a side-elevation view of a further embodiment of the invention, including radiopaque markers.

Other radiopaque markers can be provided on a stent 30g, as illustrated in FIG. 50. In addition to the marker 238 at the end of the distal anchor portion 216, a similar radiopaque marker 243 can be provided at the end of the proximal anchor portion 221. A verification marker 245 can be provided along the distal anchor portion 216 in proximity to the body portion 210. Since the mesh of the stent 30g is generally not visible under fluoroscopy, movement of the marker 238 into proximity with the verification marker 245 will provide an indication that the loop, coil, or pigtail of the anchor portion 216 has formed.

Figure 51:
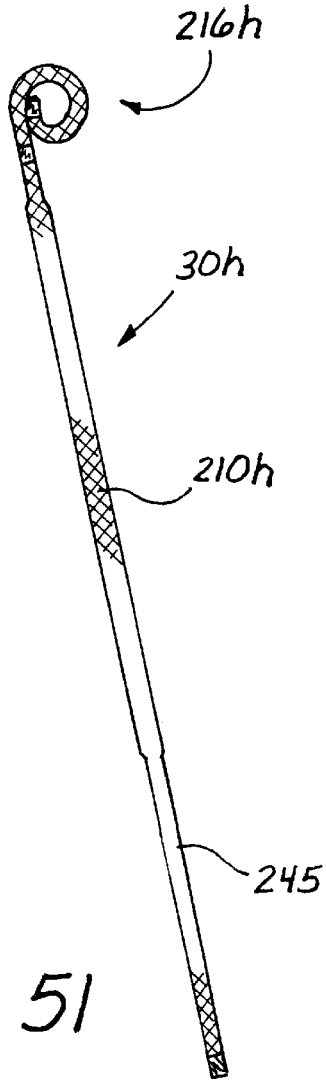
FIG. 51 is a side-elevation view of a further embodiment of the invention, including a tether.

FIG. 51 illustrates a further embodiment of the stent wherein elements of similar structure are designated by the same reference numerals followed by the lower case letter "h". In this particular embodiment, there is no anchor portion 221, but rather a generally straight tether which is attached to the proximal end of the body portion 210h. In those case where an anchor is not required in the bladder 42g, the tether 245 will merely provide a connection to the body portion 210 to ultimately facilitate removal of the stent 30h.

Figure 52:
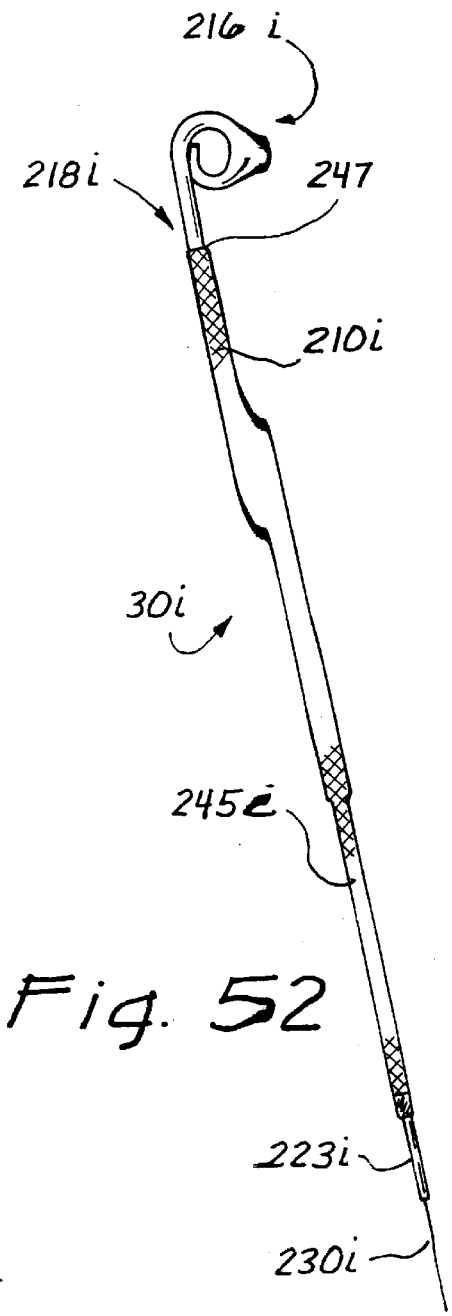
FIG. 52 is a side-elevation view of an additional embodiment, including a non-mesh pigtail anchor.

A further embodiment of the stent 30i is illustrated in FIG. 52 wherein the anchor portion 216i is formed from a material such as a silicon, urethane, or other elastomer, but is not provided with the mesh configuration. Where the anchor portion 216i is not formed integral with the body portion 210i, these elements 216i and 210i must be coupled at a junction 247 by other means such as an adhesive or a mechanical interlock. In this embodiment of FIG. 52, the junction 247 can be formed with the restriction 218i so that the positioner, such as the positioner 223 of FIG. 24, extends only to this junction 247. In this case, the guidewire 230i is relied on to straighten the anchor 216i during insertion. The positioner 223i functions to push the anchor portions 216i, and to pull the remainder of the stent 30i distal of the junction 247.

Further embodiments of the invention are illustrated in the side-elevation views of FIGS. 53, 54, 55, 56, 57, 58, 59, and 60. In these views, elements similar to those previously discussed are designated by the same reference numerals followed by the lower-case letters j, k, l, m, n, o, p, and q, respectively. For example, in the embodiment of FIG. 53, the stent is designated by the reference numeral 30j. In this embodiment, the body portion 210j and the tether 245j can be similar to those previously discussed. A distal anchor 250 can be heatset in the general configuration of a sphere 252 having a diameter such as one-half inch to one inch in certain preferred embodiments. The sphere 252 can be formed of any of the materials previously discussed, but in a preferred embodiment is formed of a mesh material which is integral with the mesh of the body portion 210j.

Since most of the patient discomfort associated with stents results from the anchors in the bladder 42 and kidney 40, the spherical anchor 250 offers considerable advantage to this embodiment of the invention. The only contact with the kidney in this case is along a hemispherical surface 254 which contacts the body portion 210j. This advantage is achieved without sacrificing the advantages of previous embodiments which provide for use of a positioner, such as the positioner 223 of FIG. 24. Tensioning the stent 30j on such a positioner causes the sphere 252 to collapse to a cylindrical, low-profile configuration facilitating insertion. Upon removal of the positioner 223 and guidewire 230 (FIGS. 46 and 47), the heatset mesh automatically expands to form the spherical anchor 250.

Figure 54:
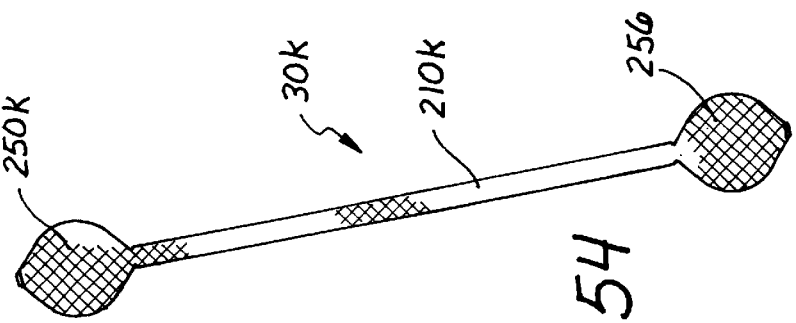
FIG. 54 is a side-elevation view of a further embodiment having multiple spherical mesh anchors.

The embodiment of FIG. 54 illustrates that the stent 30k can be formed not only with the distal spherical anchor 250k, but also a proximal spherical anchor 256.

Figure 55:
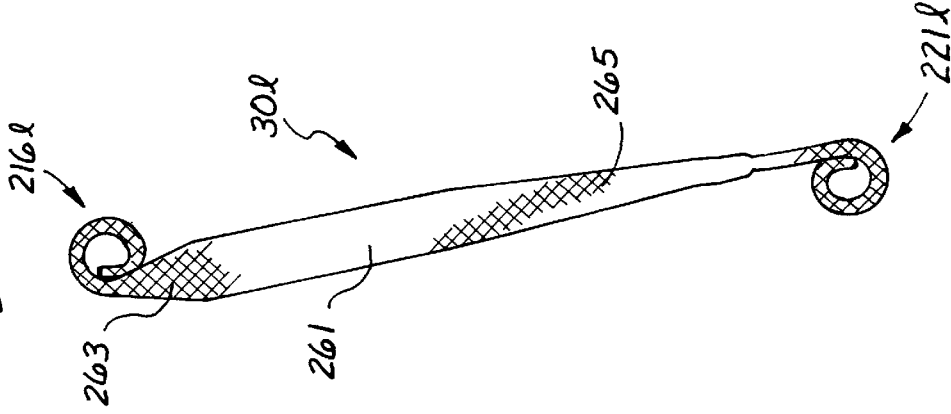
FIG. 55 is a side-elevation view of a further embodiment with a preferred body portion of the stent.

In the embodiment of FIG. 55, the stent 301 includes pigtail anchors 2161 and 2211 of the type previously discussed. In this embodiment, the body portion 2101 differs from the generally cylindrical configuration previously discussed. In this case, the body portion 2101 includes a central portion 261 which is heatset to a generally cylindrical configuration. The body portion 2101 also includes tapered portions 263 and 265 which are disposed at opposite ends of the central portion 261. The tapered portion 263 is connected between the central portion 261 and the distal anchor 2161, while the proximal tapered portion 265 is connected between the central portion 261 and the proximal end 2211. The distal taper 263 in this embodiment is provided with a relatively large taper angle making this portion 263 relatively short compared to the proximal tapered portion 265 where the taper angle is relatively small. In many of the other aspects of the stent 301, features are similar to those previously discussed which provide for low-profile insertion using a positioner, such as the positioner 223 of FIG. 24.

Figure 56:
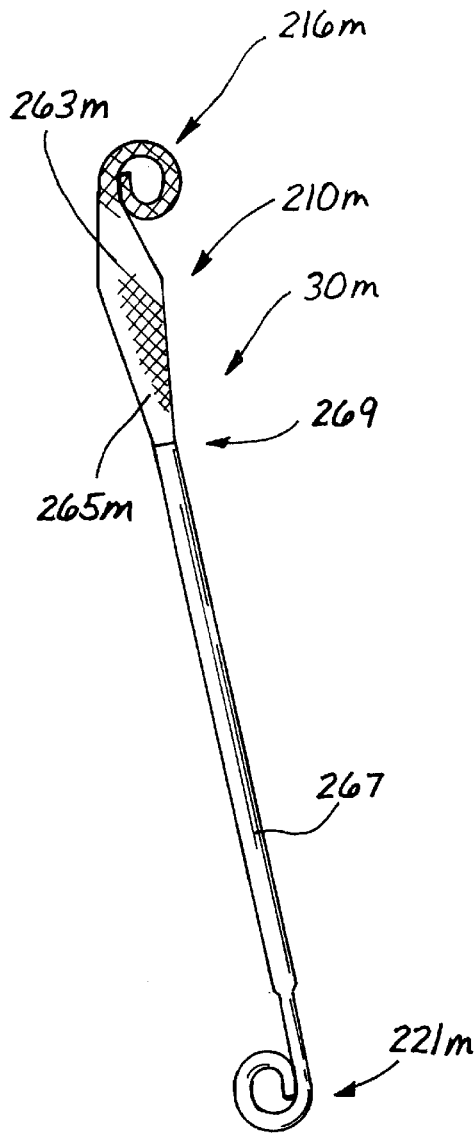
FIG. 56 is a side-elevation view of a further embodiment, including the body portion with a solid cylindrical element.

A further embodiment of the stent is illustrated in FIG. 56 and designated by the reference numeral 30m. This embodiment includes the mesh pigtail 216m, as well as a mesh body portion 210m with tapered portions 263m and 265m. In this embodiment, the body portion 210m also includes a cylindrical portion 267 which is formed of a solid material and joined to the mesh material of the tapered portion 265m at a junction 269. The cylindrical portion 267 can be formed of silicone, urethane, or other elastomer. This material can be joined to the mesh at the junction 269 by adhesive or by a mechanical, heatset interlock between the fibers of the mesh and the solid material of the cylinder 267.

Figure 57:
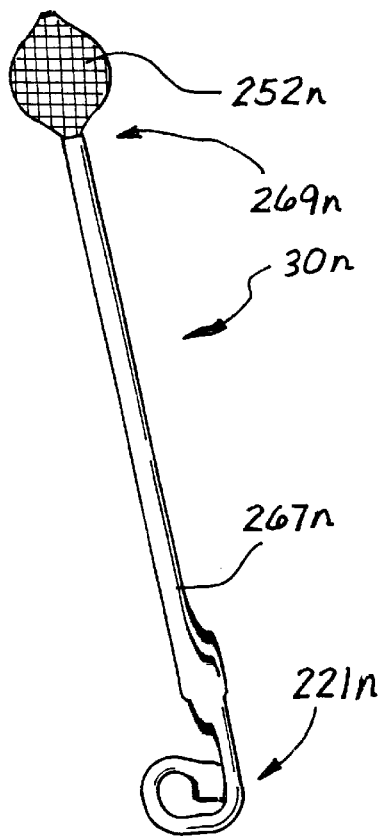
FIG. 57 is a side-elevation view of a further embodiment, including a mesh anchor and a non-mesh body portion.

The embodiment of FIG. 57 is similar to that of FIG. 56 in that it includes the cylinder 267n and proximal anchor 221n. In this embodiment, the mesh body portion 210n has been eliminated, but the distal mesh spherical anchor 252 has been retained.

Figure 53:
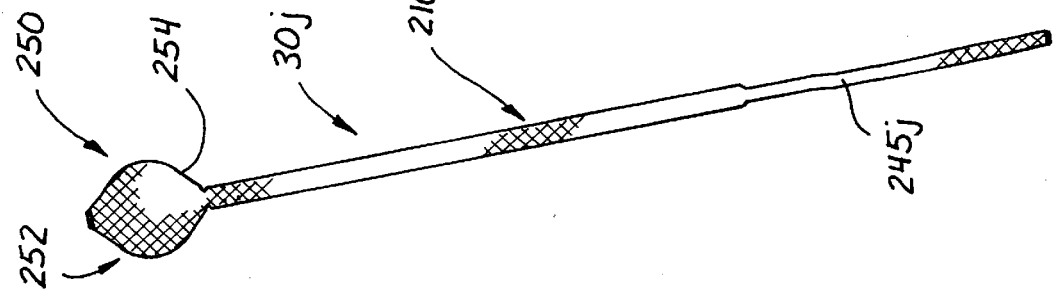
FIG. 53 is a side-elevation view of a further embodiment having an anchor with a spherical shape.
Figure 59:
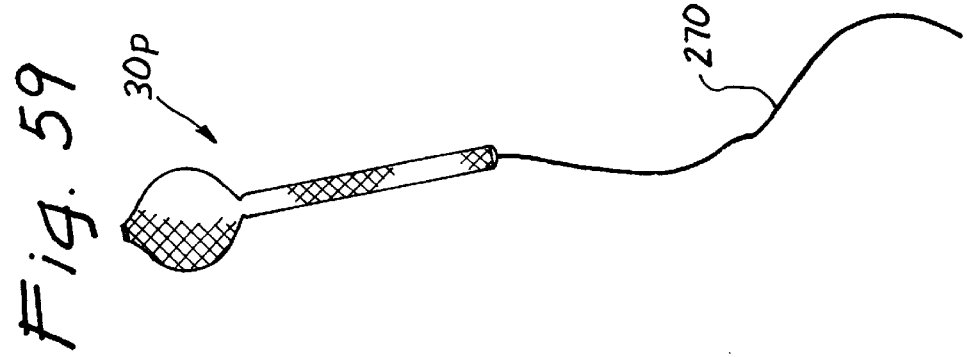
FIG. 59 is a further embodiment of the invention having a filament tether.
Figure 58:
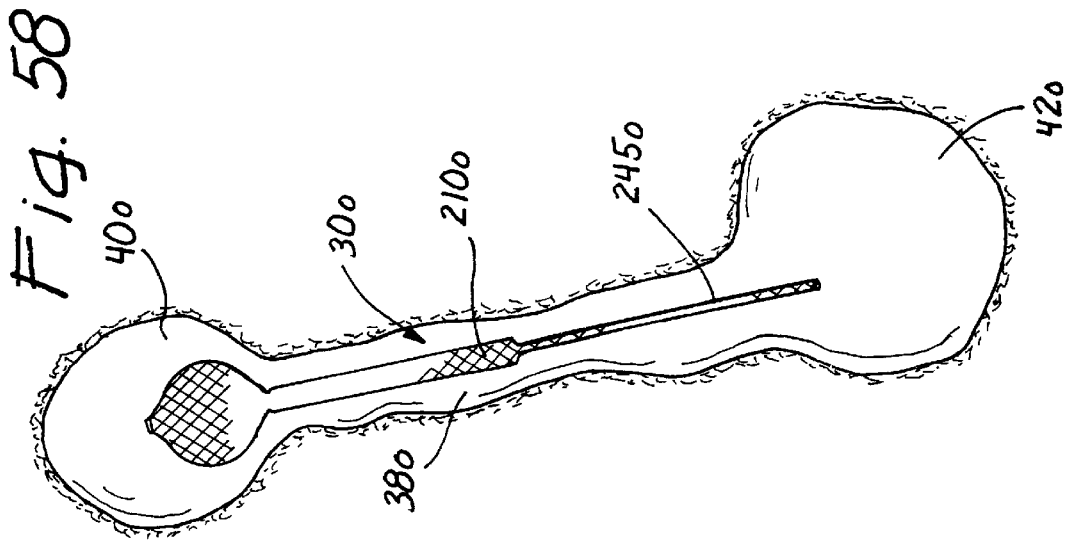
FIG. 58 is a side-elevation view of a further embodiment disposed in situ and having a body portion with an aforeshortened link.

The stent 30o illustrated in FIG. 58 combines the spherical mesh anchor 250o of the FIG. 53 embodiment, as well as the body portion 210o and tether 245o associated with the FIG. 51 embodiment. In this case, it is noted that the body portion 210 has a length which is shorter than the length of the ureter 38. Realizing that the incision is made in the upper portions of the ureter 38o, and that the features of the stent 30o are most appreciated in the vicinity of the incision, the body portion 210o of this embodiment is limited to that region. In a preferred embodiment, the shortened length of the body portion 210o is about one-half the length of the ureter 38o. Only the tether 245o extends through the proximal end of the ureter 38o and into the bladder 42o. The stent 30p illustrated in FIG. 59 is similar to that illustrated in FIG. 58, except that the tether 245o is formed as a solid shaft, string, or filament 270.

Figure 60:
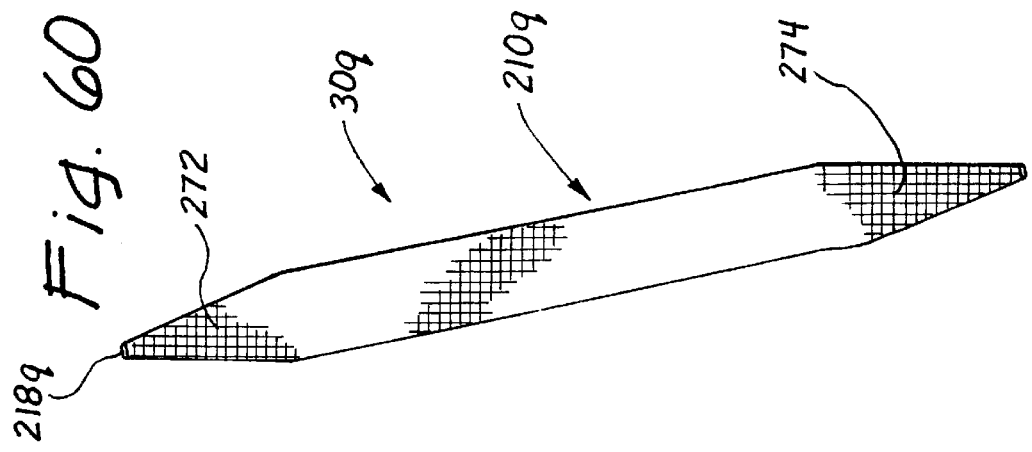
FIG. 60 is a side-elevation view of a further embodiment free of any anchor portions.

A further embodiment of the invention is illustrated in FIG. 60, where the stent 30q is free of any anchors such as the distal anchor 216 or proximal anchor 221 of the embodiments previously discussed. This embodiment can still be formed of a mesh material and provided with a body portion 210q terminating in a distal taper 272 and a proximal taper 274. At the distal end, the constriction 218q can be formed to facilitate insertion with a positioner, such as the positioner 223 of FIG. 24.

It can be seen from the foregoing discussion that various embodiments of this concept include at least one filament which is formed from a relatively strong material such as polyester. While this material may be strong and somewhat rigid, the stent 30 is provided with relatively soft characteristics due to the configuration applied to the filaments 84. Movement of the filaments 84 between the ends 32 and 34 of the stent 30 is desired not only to facilitate this soft characteristic, but also to "irritate" the wall of the conduit. This causes the conduit wall to move away from the stent 30 thereby increasing the patency of the conduit. In some cases, the stent 30 is provided with characteristics to naturally move toward a larger diameter. With these properties, the stent 30 effectively chases the wall radially outwardly to further increase the patency of the conduit.

Between the ends 32 and 34 of the stent 30, the elements 84 are free to move relative to each other between a low-profile state facilitating insertion and a high-profile state facilitating conduit patency. This relative movement of the elements 84 not only facilitates the soft characteristics preferred for the stent 30, but also results in the desired irritation of the conduit wall.

Although it is contemplated that most embodiments of the stent 30 will include elements 84 formed of the same material, this may not always be the case. In some instances, it may be desirable to form the elements 84 from different materials to provide the overall stent 30 with properties representative of each of the materials. For example, some of the elements 84 may be formed from a polyester material providing the stent with a relatively high tensile strength. Other elements may be formed of an absorbent material which can be saturated, for example, with an antibiotic, an anesthetic, an analgesic, a material to control encrustation, a radiopaque material, or any other material having medical characteristics.

The impregnation or coating of the elements 84 with drugs or chemicals offers particular advantages. For example, some procedures require such chemicals or drugs to be administered at a specific site within a body passage. When these drugs or chemicals are administered systemically, there can be concomitant and adverse side-effects. When it is desirable to administer medications, drugs, or chemicals, particularly those that are highly concentrated or powerful, a system for localizing the effect to a specific site can be particularly advantageous in avoiding the side-effects of systemic administration. To this end, an intraluminal device for local administration of the medications, drugs, or chemicals is contemplated by the present invention.

More specifically, a stent 30 having properties for absorbing and subsequently delivering or releasing a chemical or a drug is foreseen. When the stent 30 is provided with a woven or braided tubular structure, it can be inserted into a body passage for the purpose of increasing patency of that passage. The stent can be constructed solely of mono-filament fibers or a rigid polymer, as previously discussed. These fibers are generally non-absorbent. However, in an alternate embodiment, at least one of the elements can be formed of cotton, dacron, or other absorbent material. These absorbent elements can be woven with the mono-filaments elements, in a predetermined ratio facilitating delivery of an absorbed chemical, drug, or medication. The stent can then be soaked, wiped, or doped with the selective chemical or combination of chemicals or drugs. The absorbent elements may be formed as a yarn and provided with various properties including alternative rates of absorption or take-up of the chemical, as well as alternative rates of release or delivery of the chemical. This may be accomplished by blending various fibers within a single yarn element or by controlling the density of the weave or the chemical or mechanical treatment of the surface of the yarn element.

The releasing element may also be made of an absorbable material that releases the chemical or drug as the element desolves in body fluids. The agents may be time-released or bolused, depending on the properties of the fiber elements. The agents to be released or administered can be compounded so that a single woven or braided element contains a variety of agents to be delivered at defined rates and dosages over different times. Many other combinations of elements and materials will be apparent to provide the stent with selective characteristics desirable in a particular operative setting.

Although exemplary embodiments of the invention have been shown and described, many other changes, modifications, and substitutions will now be apparent to those of ordinary skill in the art, without necessarily departing from the spirit and scope of this invention as set forth in the following claims.

What is claimed is:

1. A ureteral stent adapted for disposition in a ureter and relative to a kidney, comprising:

a body portion adapted for disposition in the ureter and having the configuration of a tube with a lumen extending between a proximal end and a distal end;

an anchor portion having the configuration of a pigtail and being adapted for disposition in the kidney, the anchor portion being coupled to the body portion at the distal end of the body portion and having a hollow tubular configuration with a first end and a second end, the first end being coupled to the distal end of the body portion in fluid communication with the lumen of the body portion; and at least one of the body portion and the anchor portion being formed of a flexible mesh and being free of any other structures reinforced by the mesh.

2. The ureteral stent recited in claim 1 wherein the anchor portion is formed of the mesh.

3. The ureteral stent recited in claim 2 wherein the body portion is formed of the mesh and is integral with the mesh of the anchor portion.

4. The ureteral stent recited in claim 1, wherein the anchor portion is a first anchor portion and the stent further comprises:

a second anchor portion coupled to the proximal end of the body portion.

5. The ureteral stent recited in claim 1, further comprising:

a tether coupled at the proximal end of the body portion; and at least one of the body portion, anchor portion, and tether being formed of the mesh.

6. A ureteral stent adapted for disposition in a ureter and relative to a kidney, comprising:

a body portion adapted for disposition in the ureter and having the configuration of a tube with a lumen extending between a proximal end and a distal end;

an anchor portion adapted for disposition in the kidney and coupled to the body portion at the distal end of the body portion, the anchor portion having a hollow tubular configuration with a first end and a second end, the first end being coupled to the distal end of the body portion in fluid communication with the lumen of the body portion;

at least one of the body portion and the anchor portion being formed of a flexible mesh and being free of any other structures reinforced by the mesh; and the anchor portion having a first diameter and the body portion being heatset to a second diameter greater than the first diameter.

7. The ureteral stent recited in claim 6 wherein the anchor portion terminates at a constriction having a third diameter less than the first diameter of the anchor portion.

8. The ureteral stent recited in claim 6, wherein the anchor portion is formed of the mesh.

9. The ureteral stent recited in claim 8 wherein the body portion is formed of the mesh and is integral with the mesh of the anchor portion.

10. The ureteral stent recited in claim 6, wherein the anchor portion is a first anchor portion and the stent further comprises:

a second anchor portion coupled with the proximal end of the body portion.

11. The ureteral stent recited in claim 6, further comprising:

a tether coupled to the proximal end of the body portion; and at least one of the body portion, anchor portion, and tether being formed of the mesh.

12. A ureteral stent adapted for disposition in a ureter and relative to a kidney, comprising:

a body portion adapted for disposition in the ureter and having the configuration of a tube with a lumen extending between a proximal end and a distal end;

an anchor portion having a generally spiral configuration and being adapted for disposition in the kidney, the anchor portion having a hollow configuration and being coupled to the body portion at the distal end of the body portion in fluid communication with the lumen of the body portion; and at least one of the body portion of the anchor portion being formed of a flexible mesh and being free of any other structures reinforced by the mesh.

13. The ureteral stent recited in claim 12, wherein the anchor portion is formed of the mesh.

14. The ureteral stent recited in claim 13, wherein the body portion is formed of the mesh and is integral with the mesh of the anchor portion.

15. The ureteral stent recited in claim 12, wherein the anchor portion is a first anchor portion and the stent comprises:

a second anchor portion coupled to the proximal end of the body portion.

16. The ureteral stent recited in claim 12, further comprising:

a tether coupled to the proximal end of the body portion; and at least one of the body portion, anchor portion, and tether being formed of the mesh.

\* \* \* \* \*